United States Patent
Zwierstra et al.

(10) Patent No.: US 10,478,260 B2
(45) Date of Patent: Nov. 19, 2019

(54) ENCLOSURE FOR AN ACOUSTIC ENERGY DEVICE INCLUDING A PROBE

(71) Applicant: Neural Analytics, Inc., Los Angeles, CA (US)

(72) Inventors: Jan Zwierstra, Los Angeles, CA (US); Kiah Lesher, Los Angeles, CA (US); Lane Stith, Los Angeles, CA (US)

(73) Assignee: NEURAL ANALYTICS, INC., Los Angeles, CA (US)

( * ) Notice: Subject to any disclaimer, the term of this patent is extended or adjusted under 35 U.S.C. 154(b) by 14 days.

(21) Appl. No.: 15/952,791

(22) Filed: Apr. 13, 2018

(65) Prior Publication Data

US 2019/0314105 A1    Oct. 17, 2019

(51) Int. Cl.
| | | |
|---|---|---|
| *A61B 50/30* | (2016.01) | |
| *A61B 8/00* | (2006.01) | |
| *A61B 46/10* | (2016.01) | |
| *A61B 90/00* | (2016.01) | |

(52) U.S. Cl.
CPC ............ *A61B 50/30* (2016.02); *A61B 8/4263* (2013.01); *A61B 8/4281* (2013.01); *A61B 8/4422* (2013.01); *A61B 46/10* (2016.02); *A61B 2050/314* (2016.02); *A61B 2090/037* (2016.02); *A61B 2090/0808* (2016.02); *A61B 2090/3937* (2016.02)

(58) Field of Classification Search
CPC ....... A61B 50/30; A61B 46/10; A61B 8/4263; A61B 8/4281; A61B 8/4422; A61B 2090/3937; A61B 2090/0808; A61B 2090/037; A61B 2050/314

See application file for complete search history.

(56) References Cited

U.S. PATENT DOCUMENTS

| | | | | |
|---|---|---|---|---|
| 5,609,564 | A * | 3/1997 | Makita | A61B 1/00142 374/158 |
| 5,795,632 | A * | 8/1998 | Buchalter | A61B 8/12 206/305 |
| 6,123,454 | A * | 9/2000 | Canfield | G01J 5/021 374/158 |
| 2007/0238995 | A1 * | 10/2007 | Sui | A61B 5/02007 600/437 |
| 2010/0016707 | A1 * | 1/2010 | Amara | A61B 5/02007 600/411 |
| 2017/0128042 | A1 * | 5/2017 | Desai | A61B 8/4281 |

* cited by examiner

*Primary Examiner* — Amelie R Gillman
(74) *Attorney, Agent, or Firm* — Foley & Lardner LLP

(57) ABSTRACT

Arrangements described herein relate to systems, apparatuses, and methods for an enclosure for a device having a probe supported by a housing. The housing defines a cavity through which the probe protrudes. The probe is configured to move within the cavity. The enclosure includes a removable enclosure body. The enclosure body is configured to enclose at least a portion of the housing while covering an entirety of the cavity. The enclosure further includes a probe interaction portion in the enclosure body. The probe interaction portion is configured to be operatively engaged with the probe such that the probe is configured to transmit acoustic energy to a subject from within the enclosure.

27 Claims, 18 Drawing Sheets

ENCLOSURE FOR AN ACOUSTIC ENERGY DEVICE INCLUDING A PROBE

BACKGROUND

A device (e.g., an ultrasound or, more particularly, a transcranial Doppler (TCD) device) may include a probe (e.g., a movable, robotic probe) configured to image or measure physiological data of a subject or patient. The medical device may also include at least one camera for aiding in proper automatic alignment of the probe with respect to an anatomical feature of a human, or to properly register the medical device with respect to the anatomical feature of the human, for improving accuracy and precision of the sampled data. A housing of the medical device may also define a cavity through which the probe protrudes. The probe moves within a boundary defined by the cavity. During the operation of the probe, particles (e.g., hair) and liquid (e.g., blood and gel) may fall into the cavity, which may be hazardous to the electronic and mechanical components of the device that are exposed by the cavity.

SUMMARY

In some arrangements, an enclosure for a device is described. The device includes a probe supported by a housing. The housing defining a cavity through which the probe protrudes. The probe being configured to move within the cavity. The enclosure includes a removable enclosure body and a probe interaction portion at the enclosure body. The enclosure body is configured to enclose at least a portion of the housing while covering an entirety of the cavity. The probe interaction portion is configured to be operatively engaged with the probe such that the probe is configured to transmit acoustic energy to a subject from within the enclosure.

In some arrangements, the probe interaction portion includes a first hole that exposes at least a portion of the probe. The first hole forms a seal around the probe when the enclosure is attached to the housing.

In some arrangements, the probe interaction portion includes an inner surface of the enclosure body including an adhesive configured to attach the probe interaction portion to a surface of probe.

In some arrangements, the enclosure body includes a first portion around the first hole, the first portion including an excess material. The excess material forms a pocket around the cavity when the enclosure covers the housing. The excess material allows the probe to travel freely when the enclosure covers the housing.

In some arrangements, dimensions of the first hole are smaller than corresponding dimensions of the probe. The first portion forms the seal around the probe by providing a friction fit with the probe to prevent liquid and particles from entering into the cavity. The friction fit is created as the probe is inserted through the first hole, causing the first portion to stretch to form the seal around the probe due to differences of the dimensions of the first hole and the corresponding dimensions of the probe.

In some arrangements, the dimensions of the first hole include a first radius, the dimensions of the probe includes a second radius, and the first radius is smaller than the second radius.

In some arrangements, the enclosure body further includes a second portion different from the first portion, and the first portion and the second portion are made of different materials.

In some arrangements, the first hole is operatively engaged with the probe to form the seal around the probe via at least one of an elastic band around the first hole, a two-piece snap ring, an adhesive collar, a flap portion, and a strap.

In some arrangements, the enclosure further includes a first marker. At least one of the first marker is printed on the enclosure body. The first marker is attached to an exterior surface of the enclosure via first adhesives, the exterior surface facing away from the housing when the enclosure covers the housing. The first marker is attached to an interior surface of the enclosure body via second adhesives. The interior surface facing the housing when the enclosure covers the housing.

In some arrangements, the first marker includes a ring around the first hole. A stretchable portion of the enclosure body is between the first marker and the first hole. The stretchable portion forms the seal around the probe by providing a friction fit with the probe to prevent liquid and particles from entering into the cavity.

In some arrangements, the first marker is made of a material that provides additional rigidity to the stretchable portion.

In some arrangements, the first marker includes a gel reservoir for storing gel configured to facilitate transmission of the acoustic energy.

In some arrangements, the enclosure further includes at least one second hole configured to receive a camera of the device, and the camera protrudes from the at least one second hole when the enclosure covers the housing.

In some arrangements, the at least one second hole includes two holes, wherein the camera protrudes from one of the two holes when the enclosure covers the housing.

In some arrangements, wherein the at least one second hole is formed by cutting at least a portion of the enclosure body.

In some arrangements, the enclosure further includes at least one second marker, and each of the at least one second marker is positioned to indicate that each of the at least one second hole is for the camera, and at least one of the at least one second marker is printed on the enclosure body, the at least one second marker is attached to an exterior surface of the enclosure via first adhesives, the exterior surface facing away from the housing when the enclosure is attached to the housing, and the at least one second marker is attached to an interior surface of the enclosure body via second adhesives, the interior surface facing the housing when the enclosure is attached to the housing.

In some arrangements, the enclosure further includes a fastening mechanism configured to removably secure the enclosure to the housing, wherein the fastening mechanism includes at least one of an elastic band, a hook-and-loop fastener (e.g., Velcro®), adhesive strips, and strings.

In some arrangements, the enclosure further includes a fastening base configured to removably secure the enclosure to the housing, wherein the fastening base includes an adhesive base having a shape that corresponds to the cavity.

In some arrangements, the enclosure body is configured to bulge in at least one of an outward direction away from the cavity or an inward direction toward the cavity.

In some arrangements, the fastening base is made from a foam and is configured to be removably secured to a front surface of the housing such that at least a portion of the front surface of the housing is uncovered by the enclosure body.

In some arrangements, a perimeter of the fastening base is greater than a perimeter of the cavity such that the fastening base surrounds the cavity when the fastening base is removably secured to the housing.

In some arrangements, the enclosure further includes a marker positioned to indicate that the first hole is for the probe, two second holes configured to receive a camera of the device, and a fastening mechanism configured to removably secure the enclosure to the housing. The enclosure body is configured as a disposable bag having a substantially rectangular shape. The first hole is positioned in an approximated center of the substantially rectangular shape. The marker is a ring that is concentric with the first hole. Each of the second holes is formed by cutting off a corner of the substantially rectangular shape. The fastening mechanism is at an edge of the substantially rectangular shape.

In some arrangements, the enclosure body includes two or more tabs. Each of the two or more tabs includes adhesives. The two or more tabs are configured to releasably attach to the housing via the adhesives.

In some arrangements, the enclosure body is made of at least one biocompatible material suitable for contacting a human body, and the at least one biocompatible material includes one or more of polyethylene (PE), polypropylene (PE), polycarbonate (PC), polyurethane (PU), polyetherimide (PEI), polyvinyl chloride (PVC), and polyether ether ketone (PEEK).

In some arrangements, the enclosure body is made of an elastic material that can be form-fitted to the portion of the housing when the enclosure covers the housing.

In some arrangements, the enclosure body is made of a material that provides ingress protection against liquid and particles to the cavity.

In some arrangements, a method for providing an enclosure for a device is described. The enclosure includes a probe supported by a housing. The housing defining a cavity through which the probe protrudes. The probe being configured to move within the cavity. The method includes providing a removable enclosure body and providing a probe interaction portion at the enclosure body. The enclosure body is configured to enclose at least a portion of the housing while covering an entirety of the cavity. The probe interaction portion is configured to be operatively engaged with the probe such that the probe is configured to transmit acoustic energy to a subject from within the enclosure.

In some arrangements, a device includes a probe, a housing supporting the probe and defining a cavity through which the probe protrudes, the probe configured to move within the cavity, a disposable enclosure. The disposable enclosure includes a removable enclosure body and a probe interaction portion at the enclosure body. The enclosure body is configured to enclose at least a portion of the housing while covering an entirety of the cavity. The probe interaction portion is configured to be operatively engaged with the probe such that the probe is configured to transmit acoustic energy to a subject from within the enclosure.

BRIEF DESCRIPTION OF THE FIGURES

Features and aspects of arrangements will become apparent from the following description and the accompanying example arrangements shown in the drawings, which are briefly described below.

DETAILED DESCRIPTION

Figure 1A:
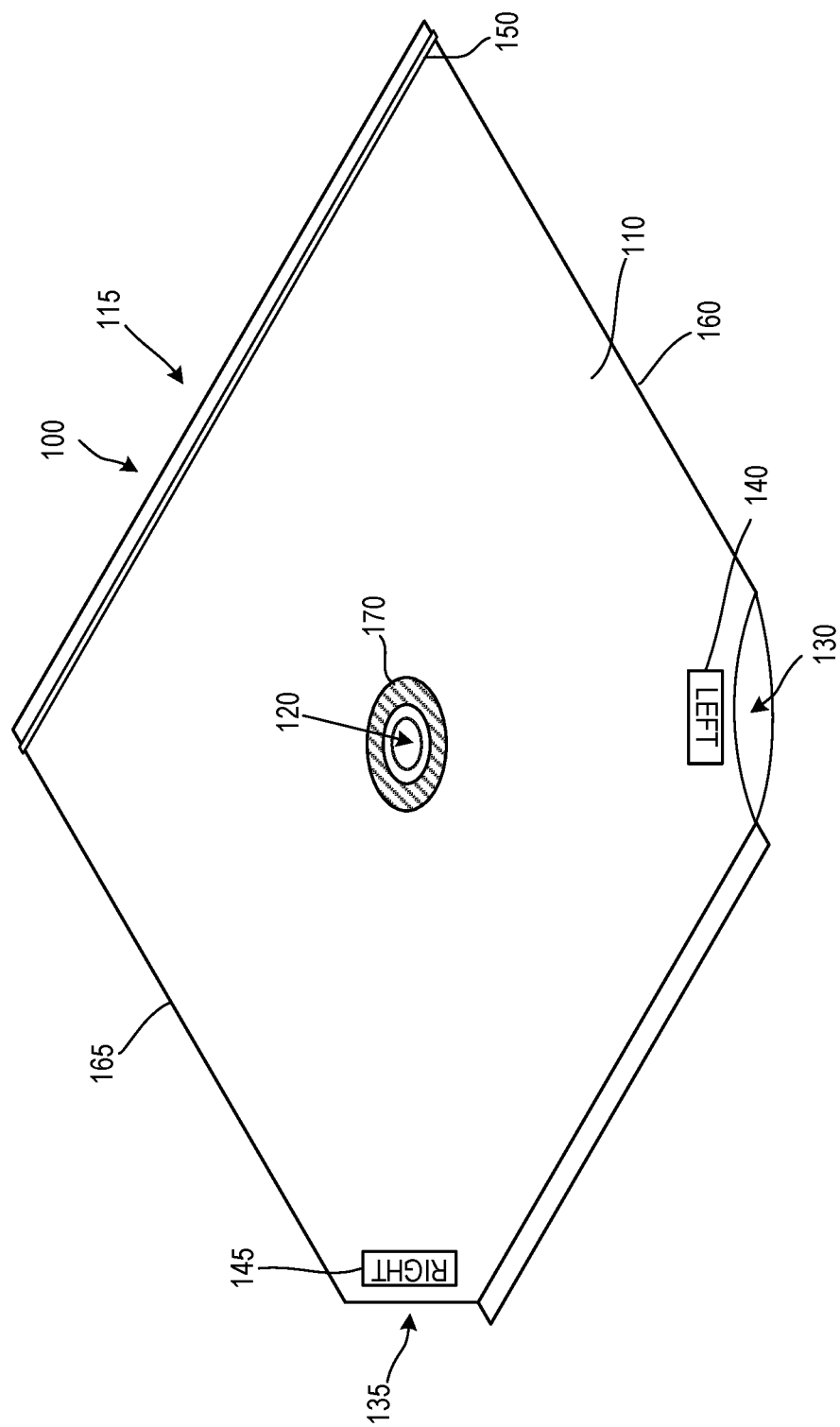
FIG. 1A shows a perspective view of an enclosure for covering a device including a probe according to various arrangements.
Figure 1B:
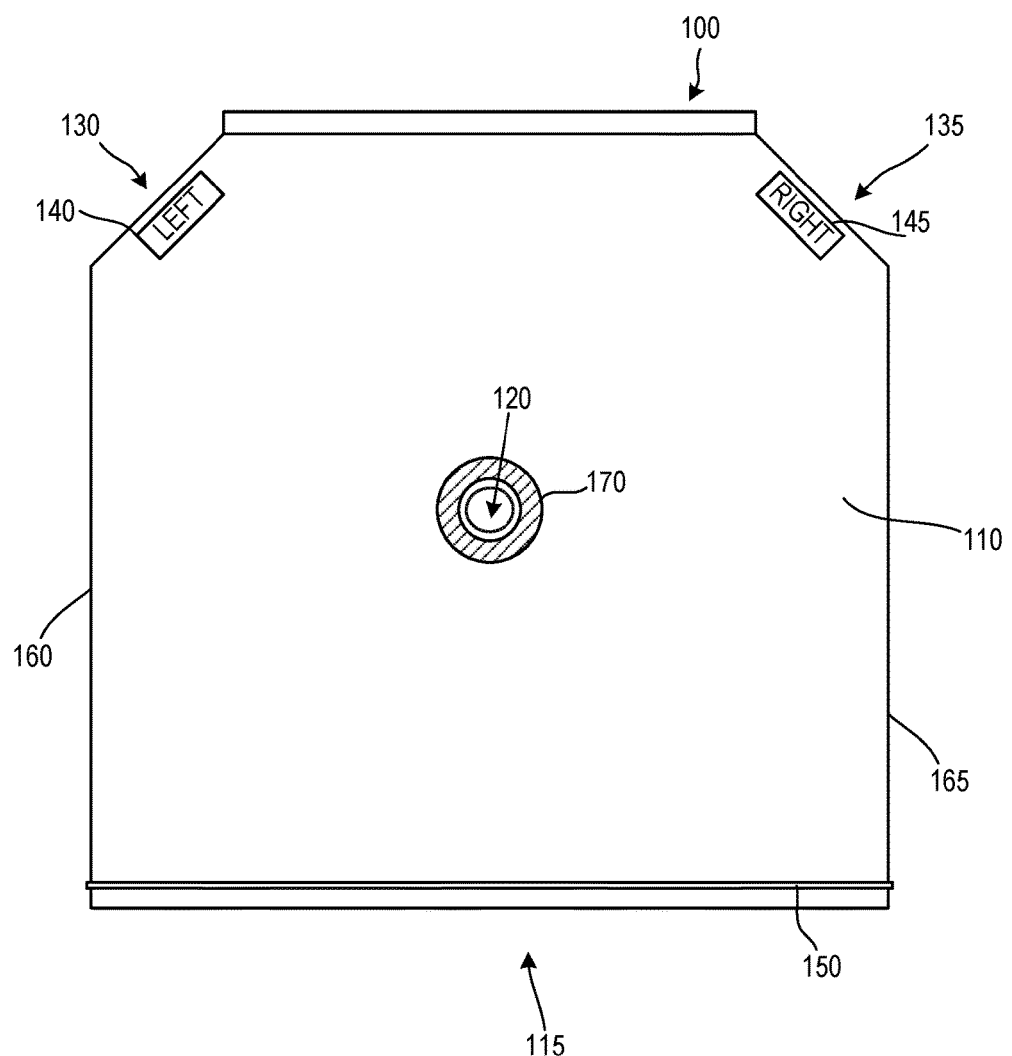
FIG. 1B shows a front view of an enclosure for covering a device including a probe according to various arrangements.
Figure 1C:
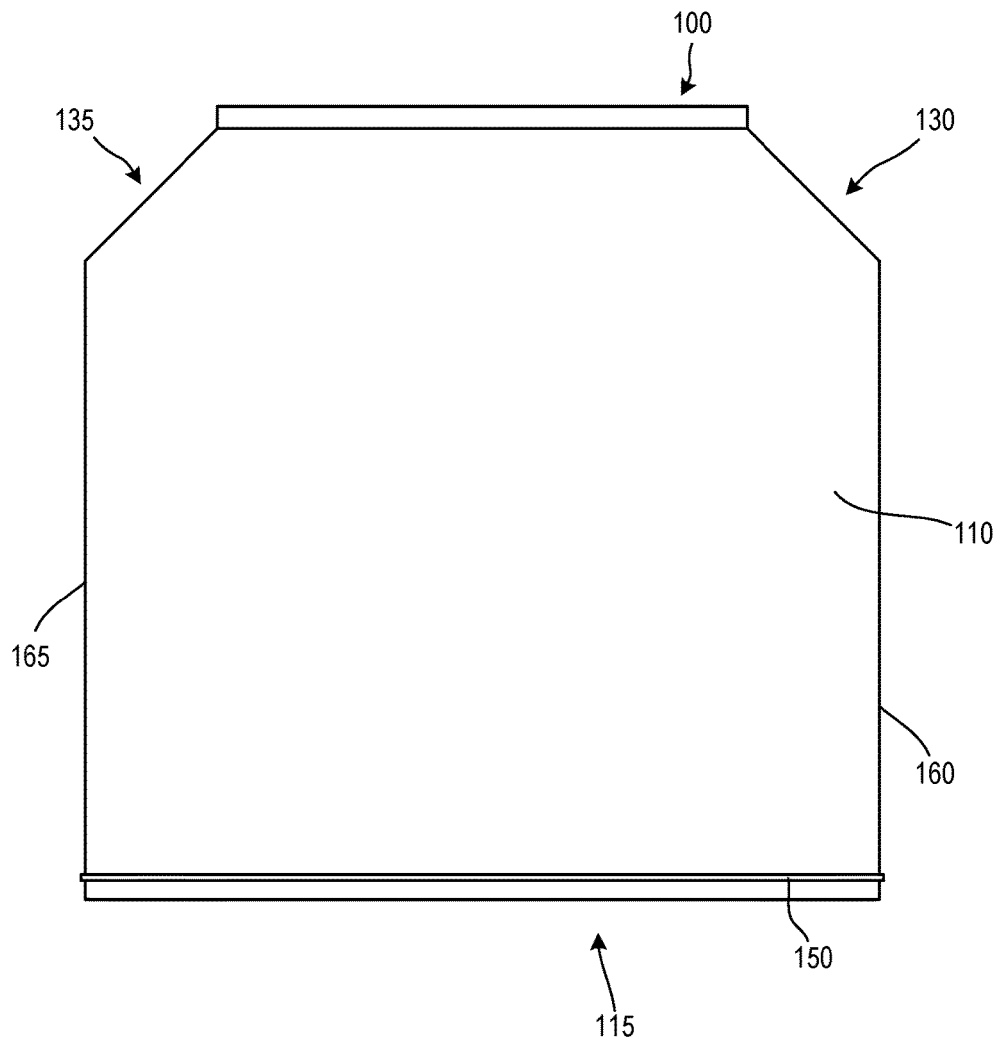
FIG. 1C shows a back view of an enclosure for covering a device including a probe according to various arrangements.
Figure 1D:
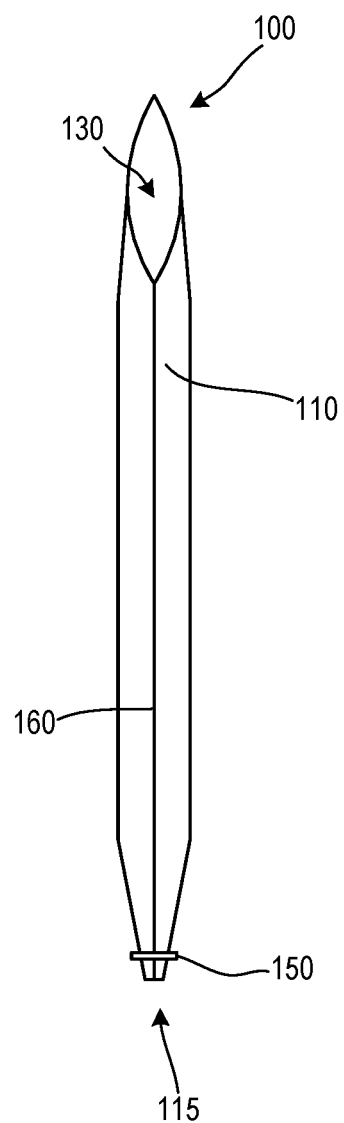
FIG. 1D shows a side view of an enclosure for covering a device including a probe according to various arrangements.
Figure 1E:
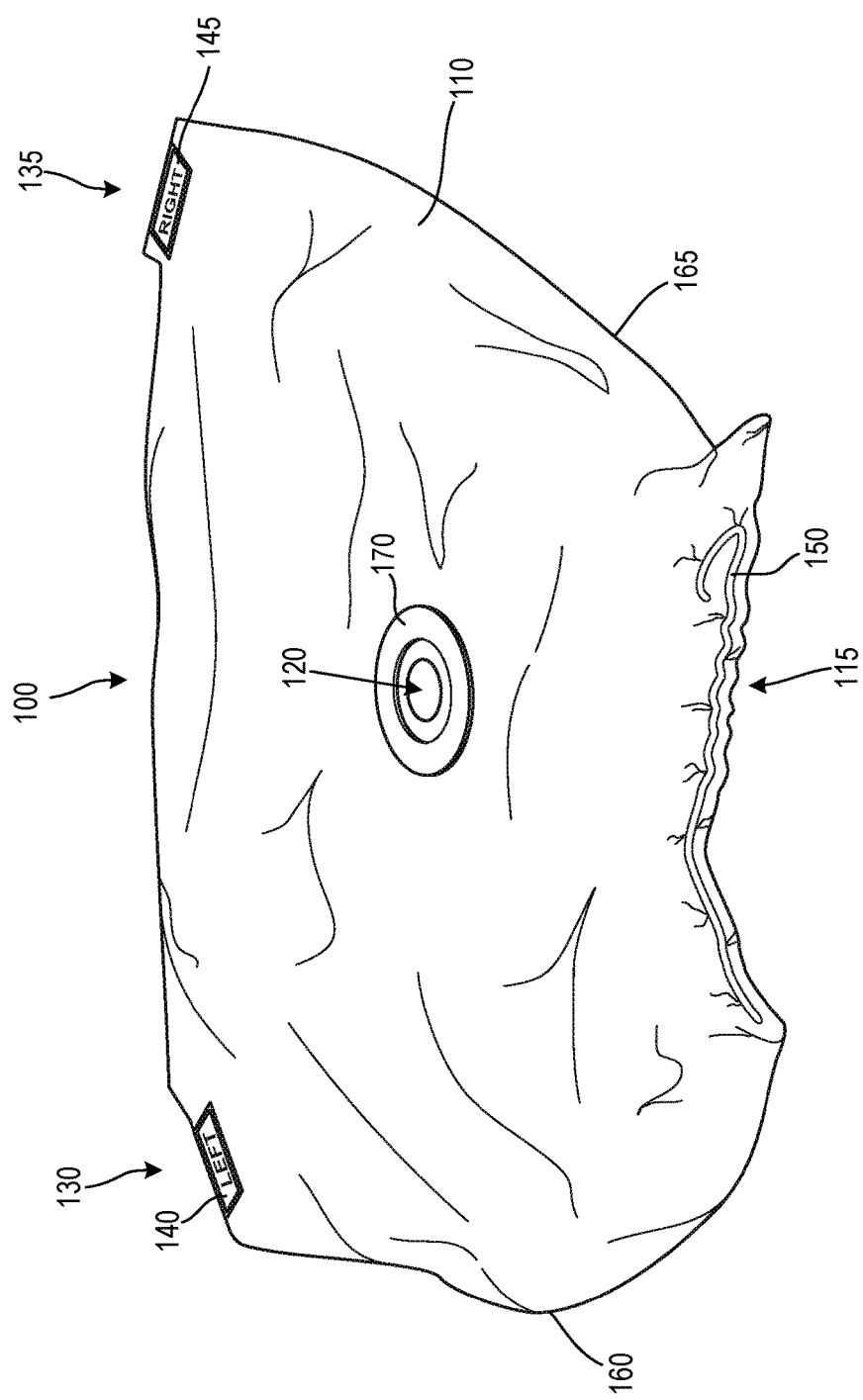
FIG. 1E shows a perspective view of an enclosure (in a resting state) for covering a device including a probe according to various arrangements.
Figure 1F:
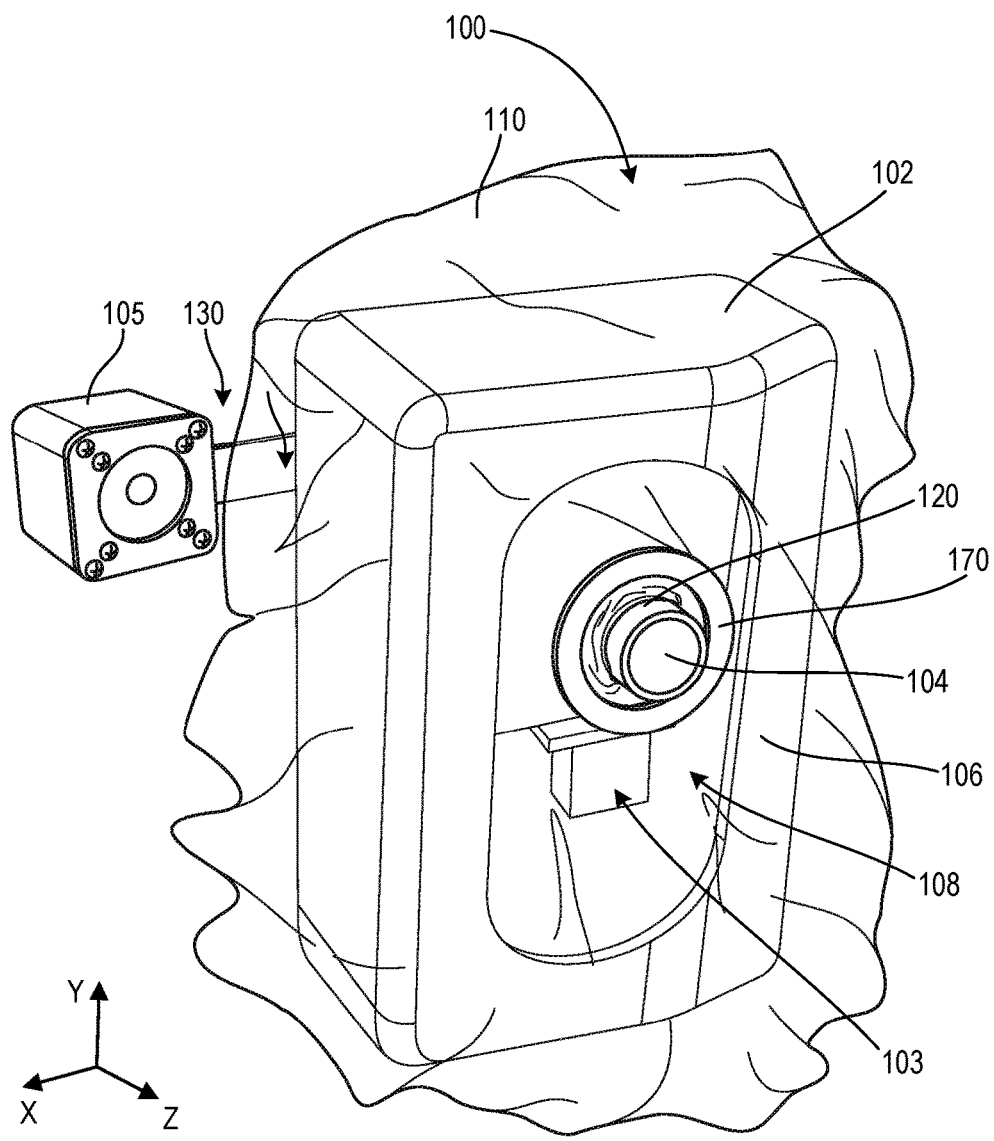
FIG. 1F shows an enclosure covering a device including a probe according to various arrangements.

The detailed description set forth below in connection with the appended drawings is intended as a description of various configurations and is not intended to represent the only configurations in which the concepts described herein may be practiced. The detailed description includes specific details for providing a thorough understanding of various concepts. However, it will be apparent to those skilled in the art that these concepts may be practiced without these specific details. In some instances, well-known structures and components are shown in block diagram form in order to avoid obscuring such concepts.

In the following description of various arrangements, reference is made to the accompanying drawings which form a part hereof and in which are shown, by way of illustration, specific arrangements in which the arrangements may be practiced. It is to be understood that other arrangements may be utilized, and structural changes may be made without departing from the scope of the various arrangements disclosed in the present disclosure.

Arrangements described herein relate to systems, apparatuses, and methods for providing a disposable or permanently fixed enclosure for covering at least a portion of a housing of a device including a probe. The housing includes a cavity through which a probe protrudes. The probe moves within a boundary defined by the cavity. The enclosures disclosed herein are configured to seal or otherwise enclose the housing to prevent particles (e.g., hair) and/or liquid (e.g., blood and gel) from entering into the cavity, thus improving performance and longevity of the device including the probe.

FIGS. 1A-1G show an enclosure 100 configured to cover a device 102 including a probe 104 according to various arrangements. Referring to FIGS. 1A-1G, in some examples, the device 102 including the probe 104 can be an ultrasound device (e.g., a TCD ultrasound device) configured to emit and measure acoustic waves in a subject (e.g., in a head of the subject). The device 102 includes the at least one probe 104 (e.g., at least one ultrasound probe) configured to emit and measure ultrasound acoustic energy. For example, the device 102 including the probe 104 can automatically locate the middle cerebral artery (MCA) of a brain of a subject, in some arrangements. In some arrangements, the probe 104 is positioned in a temporal window region (temple) of the head to collect the ultrasound data. In other arrangements, the probe 104 can be positioned over different acoustic windows such as, but not limited to, the transorbital window or the suboccipital window. A lubricating gel can be applied between the head and the probe 104 to facilitate and improve acoustic transmission.

Further disclosure regarding examples of the probe 104 and the device 102 can be found in non-provisional patent application Ser. No. 15/399,648, titled ROBOTIC SYSTEMS FOR CONTROL OF AN ULTRASONIC PROBE, and filed on Jan. 5, 2017, and in non-provisional patent application Ser. No. 15/853,433, titled HEADSET SYSTEM, and filed Dec. 22, 2017, which are incorporated herein by reference in their entirety. In some arrangements, the device 102 includes manually operated probes, as opposed to automatically or robotically-operated probes.

In some arrangements, the device 102 includes robotics 103 configured to control positioning of the probe 104. In other words, the robotics 103 are configured to translate the probe 104 along a surface of the head and to move the probe 104 with respect to (e.g., toward and away from) the head along various axes in the Cartesian, spherical, and rotational coordinate systems. For example, the robotics 103 can include a multiple degree-of-freedom (DOF) TCD transducer positioning system with motion planning. In some arrangements, the robotics 103 are capable of supporting two, three, four, five, or six DOF movements of the probe 104 with respect to the head. In some instances, the robotics 103 can translate in X and Y axes (e.g., along a surface of the head) to locate a temporal window region, and in Z-axis with both force and position feedback control to both position and maintain the appropriate force against the skull/skin to maximize signal quality by maintaining appropriate contact force. Two angular DOF (e.g., pan and tilt) may be used to maximize normal insonation of blood vessels to maximize velocity signals.

In some arrangements, an end of the probe 104 is operatively coupled to or otherwise interfaces with the robotics 103. The robotics 103 include components, such as but not limited to a motor assembly and the like for controlling the positioning of the probe 104 (e.g., controlling Z-axis pressure, controlling a position on a plane defined by the X-axis and the Y-axis, normal alignment, or the like of the probe 104). In some arrangements, the registration of the probe 104 against the head can be accomplished using the robotics 103 to properly position and align the probe 104 in the manner described. For example, a camera 105 can register the device 102 to determine the relevant workspace of the probe 104. Further disclosure regarding registration of the device 102 using the camera 105 can be found in provisional patent application No. 62/558,804, titled SYSTEMS AND METHODS FOR REGISTERING HEADSET SYSTEM, and filed on Sep. 14, 2017.

In some arrangements, the probe 104 includes a first end and a second end that is opposite to the first end. The first end includes a concave surface that is configured to be adjacent to or contact a scanning surface on the head. The concave surface is configured to correspond to a particular pitch to focus generated energy towards the scanning surface. In some arrangements, the device 102 is a TCD apparatus such that the first end of the probe 104 is configured to be adjacent to or contact and align along a side of the head. The first end of the probe 104 is configured to provide ultrasound wave emissions from the first end and directed into the head (e.g., toward the brain). For example, the first end of the probe 104 can include a transducer (such as, but not limited to, an ultrasound transducer, TCD, transcranial color-coded sonography (TCCS), or acoustic ultrasound transducer array such as sequential arrays or phased arrays) that emits acoustic energy capable of penetrating windows in the skull/head or neck. In other arrangements, the probe 104 is configured to emit other types of waves such as but not limited to, infrared (IR), near-infrared spectroscopy (NIRS), electro-magnetic, x-rays, or the like.

In some arrangements, the second end of the probe 104 is coupled to the robotics 103. In some arrangements, the second end of the probe 104 includes a threaded section along a portion of the body of the probe 104. The second end is configured to be secured in the robotics 103 via the threads (e.g., by being screwed into the robotics 103). In other arrangements, the probe 104 is secured in the robotics 103 by any other suitable connecting means, such as but not limited to welding, adhesive, one or more hooks/latches, one or more separate screws, press fittings, or the like.

In some arrangements, the camera 105 is configured to capture one or more images of a subject's head. From the captured one or more images, the subject's head can be registered by the device 102. That is, the device 102 can initially position the probe 104 (e.g., using the robotics 103) for subsequent operations of the device 102 on the subject's head. By doing so, the device 102 restricts a workspace of the probe 104 to certain boundaries during operation of the device 102. As shown, the workspace with respect to a plane defined by the X-axis and Y-axis corresponds to a plane defined by a cavity 108 of a housing 106 of the device 102. In other words, the probe 104 is configured to move within the cavity 108.

In some arrangements, the camera 105 is any suitable image capturing device for taking images or videos of a subject's head. For example, the camera 105 can have any suitable resolution and focal length for capturing desired images relied on to register a subject's head (e.g., about 5 megapixels and about 4 millimeter (mm) focal length). In particular arrangements, the resolution and/or the focal length of the camera 105 is fixed. In other arrangements, the resolution and/or the focal length are variable. In some arrangements, the camera 105 is mounted on the housing 106 and can extend from the housing 106 (e.g., in the X-axis, Y-axis, Z-axis, or a combination thereof). In some arrangements, the camera 105 is adjustable with respect to the housing 106, as the camera 105 can pivot, rotate, shift, and otherwise move with respect to the housing 106. In other arrangements, the camera 105 is fixed to the housing 106.

In some arrangements, the camera 105 is positioned such that particular anatomical locations of a subject's head are within a field of view of the camera 105, such that the device 102 and the enclosure 100 do not obstruct the field of view of the camera 105. For example, in some arrangements, the subject's tragus and eye (e.g., corner of the subject's eye) are visible to the camera 105 when the subject's head is held within a headset system. In some arrangements, the relative location and rotation of the camera 105 relative to the workspace of the probe 104 and the robotics 103 is a known and fixed parameter that can be utilized to register the device 102 with respect to a subject's head. In further arrangements, an exposure time of the camera 105 is adjustable (e.g., by an operator).

In some arrangements, the device 102 includes a controller (not shown) for controlling operations (including registering the device 102, controlling the robotics 103 to move the probe 104, capturing data with the probe 104), processing data, executing input commands, providing results, and the like. The controller includes a processing circuit having a processor and a memory. In some arrangements, the processor can be implemented as a general-purpose processor and is coupled to the memory. The processor includes any suitable data processing device, such as a microprocessor. In the alternative, the processor includes any suitable electronic processor, controller, microcontroller, or state machine. In some arrangements, the processor is implemented as a combination of computing devices (e.g., a combination of a Digital Signal Processor (DSP) and a microprocessor, a plurality of microprocessors, at least one microprocessor in conjunction with a DSP core, or any other such configuration). In some arrangements, the processor is implemented as an Application Specific Integrated Circuit (ASIC), one or more Field Programmable Gate Arrays (FPGAs), a Digital Signal Processor (DSP), a group of processing components, or other suitable electronic processing components.

In some arrangements, the memory includes a non-transitory processor-readable storage medium that stores processor-executable instructions. In some arrangements, the memory includes any suitable internal or external device for storing software and data. Examples of the memory include but are not limited to, Random Access Memory (RAM), Read-Only Memory (ROM), Non-Volatile RAM (NVRAM), flash memory, floppy disks, hard disks, dongles or other Recomp Sensor Board (RSB)-connected memory devices, or the like. The memory can store an Operating System (OS), user application software, and/or executable instructions. The memory can also store application data, such as an array data structure. In some arrangements, the memory stores data and/or computer code for facilitating the various processes described herein.

As used herein, the term "circuit" can include hardware structured to execute the functions described herein. In some arrangements, each respective circuit can include machine-readable media for configuring the hardware to execute the functions described herein. The circuit can be embodied as one or more circuitry components including, but not limited to, processing circuitry, network interfaces, peripheral devices, input devices, output devices, sensors, etc. In some arrangements, a circuit can take the form of one or more analog circuits, electronic circuits (e.g., integrated circuits (IC), discrete circuits, system on a chip (SOCs) circuits, etc.), telecommunication circuits, hybrid circuits, and any other suitable type of circuit. In this regard, the circuit can include any type of component for accomplishing or facilitating achievement of the operations described herein. For example, a circuit as described herein can include one or more transistors, logic gates (e.g., NAND, AND, NOR, OR, XOR, NOT, XNOR, etc.), resistors, multiplexers, registers, capacitors, inductors, diodes, wiring, and so on.

The circuit can also include one or more processors communicatively coupled to one or more memory or memory devices. In this regard, the one or more processors can execute instructions stored in the memory or can execute instructions otherwise accessible to the one or more processors. In some arrangements, the one or more processors can be embodied in various ways. The one or more processors can be constructed in a manner sufficient to perform at least the operations described herein. In some arrangements, the one or more processors can be shared by multiple circuits (e.g., a first circuit and a second circuit can comprise or otherwise share the same processor which, in some example arrangements, can execute instructions stored, or otherwise accessed, via different areas of memory). Alternatively, or additionally, the one or more processors can be structured to perform or otherwise execute certain operations independent of one or more co-processors. In other example arrangements, two or more processors can be coupled via a bus to enable independent, parallel, pipelined, or multi-threaded instruction execution. Each processor can be implemented as one or more general-purpose processors, ASICs, FPGAs, DSPs, or other suitable electronic data processing components structured to execute instructions provided by memory. The one or more processors can take the form of a single core processor, multi-core processor (e.g., a dual core processor, triple core processor, quad core processor, etc.), microprocessor, etc. In some arrangements, the one or more processors can be external to the apparatus, for example, the one or more processors can be a remote processor (e.g., a cloud-based processor). Alternatively, or additionally, the one or more processors can be internal and/or local to the apparatus. In this regard, a given circuit or components thereof can be disposed locally (e.g., as part of a local server, a local computing system, etc.) or remotely (e.g., as part of a remote server such as a cloud-based server). To that end, a circuit, as described herein can include components that are distributed across one or more locations.

The circuit can also include electronics for emitting and receiving acoustic energy such as a power amplifier, a receiver, a low noise amplifier or other transmitter receiver components. In some arrangements, the electronics are an ultrasound system. In some arrangements, the system is comprised of a headset which is used to adjust the position of a probe such as a TCD ultrasound probe. The headset can be configured manually or use an automated robotic system to position the probe over a desired location on the head. The probe transmits and receives acoustic energy which is controlled by an electronic circuit. The electronic circuit has an analog circuit component such as a power amplifier which sends a signal to the probe. The probe than receives the signal which is amplified by an analog low noise amplifier either within the probe or in the analog circuit. Both the transmitted and received signals may be digitized by the circuit. In some arrangements, the send and receive chain may be made up of entirely digital components.

An example system for implementing the overall system or portions of the arrangements can include a general-purpose computer, including a processing unit, a system memory, and a system bus that couples various system components including the system memory to the processing unit. Each memory device can include non-transient volatile storage media, non-volatile storage media, non-transitory storage media (e.g., one or more volatile and/or non-volatile memories), etc. In some arrangements, the non-volatile media may take the form of ROM, flash memory (e.g., flash memory such as NAND, 3D NAND, NOR, 3D NOR, etc.), Electrically Erasable Programmable Read-Only Memory (EEPROM), Magnetoresistive Random Access Memory (MRAM), magnetic storage, hard discs, optical discs, etc. In other arrangements, the volatile storage media can take the form of RAM, Thyristor Random Access Memory (TRAM), Z-Capacitor Random Access Memory (ZRAM), etc. Combinations of the above are also included within the scope of machine-readable media. In this regard, machine-executable instructions comprise, for example, instructions and data which cause a general-purpose computer, special purpose computer, or special purpose processing machines to perform a certain function or group of functions. Each respective memory device can be operable to maintain or otherwise store information relating to the operations performed by one or more associated circuits, including processor instructions and related data (e.g., database components, object code components, script components, etc.), in accordance with the example arrangements described herein.

As shown, the housing 106 houses and protects various electronic and mechanical components of the device 102, including the robotics 103, a part of the probe 104, the controller/circuits, and the like. The housing 106 is made from any suitable rigid material, such as, but not limited to, hard plastic, metals, aluminum, steel, titanium, magnesium, various alloys, rigid plastics, composites, carbon fiber, fiber glass, expanded foam, compression molded foam, stereolithography (SLA) or Fused Deposition Modeling (FDM)-made materials, Reaction Injection Molding (RIM) molding, acrylonitrile butadiene styrene (ABS), thermoplastic olefin (TPO), nylon, polyvinyl chloride (PVC), fiber reinforced resins, or the like.

The housing 106 defines the cavity 108 within which the probe 104 can be moved by the robotics 103 and from which the probe 104 extends for scanning a subject. The cavity 108 defines a boundary within which the probe 104 can move. As shown, the cavity 108 is located on a substantially flat surface of the housing 106. In other arrangements, the cavity 108 can be located on a surface that may have more curvature than shown in the FIGS. In some examples, the cavity 108 corresponds to a plane defined by the X-axis and the Y-axis, where the plane may also define at least a portion of the surface of the housing 106. Further, the probe 104 can extend or retract along the Z-axis (e.g., towards and away from the device 102). The extension of the probe 104 and sizes of other components (e.g., the robotics 103 and other electronic components) along the Z-axis may define a depth of the housing 106 through the cavity 108. While the cavity 108 is shown to be located at a substantially center location of the substantially flat surface of the housing 106, one of ordinary skill in the art can appreciate that the cavity 108 can be located in any suitable location of one or more surfaces of the housing 106 that fits for intended operations (e.g., movements) of the probe 104. The shape and size of the cavity 108 may be configured based on the intended operations of the probe 104. For example, as shown, the cavity 108 has a substantially oval shape with two parallel straight edges to allow the probe 104 to move therein. In other examples, the cavity 108 may have any other suitable shape such as but not limited to, oval, circle, rectangle, square, hexagon, and the like. Furthermore, the size of the cavity 108 approximates at least a portion of a subject, the physiological data for which is gathered by the probe 104. For example, the cavity 108 may be at least as large as or larger than a temporal window region (temple) of the head of the subject. In that regard, the size, position, and shape of the cavity 108 define a workspace of the probe 104. The cavity 108 may expose components of the device 102. The enclosure 100 may be configured to prevent liquid and particles from entering into the cavity 108. The enclosure 100 may be disposable (i.e., configured to be discarded after one or more uses) in some arrangements.

In some arrangements, the enclosure 100 includes an enclosure body 110. The enclosure body 110 is configured to cover the cavity 108 when the enclosure 100 is attached, fastened, or otherwise coupled to the housing 106. The enclosure body 110 is configured to enclose at least a portion of the housing 106. In that regard, the enclosure body 110 is made of a material that provides ingress protection against liquid (e.g., blood, sweat, and water) and particles (e.g., dust and hair) to the cavity 108. An example of a relevant ingression protection rating met by the material of the enclosure body 110 is Ingression Protection Rating (IPxx). In some arrangements, the enclosure body 110 is made of an elastic material that can be form-fitted to at least a portion of the housing 106 when the enclosure 100 is attached to the housing 106. Furthermore, in some arrangements, the enclosure body 110 is made of a biocompatible material suitable for contacting a human body (e.g., the head of the subject). An example of a relevant biocompatibility standard met by the material of the enclosure body 110 is the ISO 10993-1 standard. Moreover, in some arrangements, the enclosure body 110 is made of a lightweight material or an ultra-lightweight material, to impose less stress on the robotics 103 when the probe 104 is moved.

Therefore, in considering ingress protection, elasticity, biocompatibility, and weight, the enclosure body 110 can be made from a material such as but not limited to, polyethylene (PE), polypropylene (PE), polycarbonate (PC), polyurethane (PU), polyetherimide (PEI), PVC, and polyether ether ketone (PEEK) in some examples. In other examples, the enclosure body 110 can be made from a layer of thin silicone, biocompatible waterproof fibers or fabric, a medical curtain (e.g., a PE curtain), treated paper, Tyvek®, and the like.

The enclosure 100 (e.g., the enclosure body 110) defines a first hole 120. The first hole 120 is configured to operatively engage the probe 104 and expose a portion of the probe 104 that extends from the enclosure 100 through the first hole 120. For example, the portion of the probe 104 that is exposed includes the first end that has a concave surface configured to be adjacent to or to contact a scanning surface (e.g., on a head of a subject). The probe 104 can be inserted through the hole 120 to expose the portion of the probe 104.

In some arrangements, the first hole 120 forms a seal around the probe 104 when the enclosure 100 is attached, fastened, or otherwise coupled to the housing 106, and when the probe 104 is inserted through the first hole 120. In one example, dimensions (e.g., a radius) of the first hole 120 are smaller than corresponding dimensions (e.g., a radius) of the probe 104. A portion of the enclosure body 110 surrounding the first hole 120 forms the seal around the probe 104 by providing a friction fit with the probe 104 to prevent liquid and particles from entering into the cavity 108 (e.g., such that liquids or particles cannot enter between the probe 104 and the portion of the enclosure body 110 defining the first hole 120). The friction fit is formed as the probe 104 is inserted through the first hole 120, causing the portion of the enclosure body 110 surrounding the first hole 120 to stretch along the probe 104 due to differences of the dimensions of the first hole 120 and the corresponding dimensions of the probe 104, forming the seal. For example, the probe 104 having a larger radius than the first hole 120 can be forced through the first hole 120 such that the enclosure body 110 surrounding the first hole 120 is tightly affixed to the probe 104 when the enclosure 100 is properly fitted over the device 102 (e.g., such that the seal formed between the probe 104 and the enclosure 100 is liquid and particle-impermeable).

In some arrangements, when the enclosure 100 is attached, fastened, or otherwise coupled to the housing 106 and when the probe 104 is inserted through the first hole 120, the portion surrounding and around the first hole 120 corresponds to extra or excess material of the enclosure body 110. The excess material forms a pocket-like volume to allow the portion surrounding and around the first hole 120 to move freely along with movement of the probe 104. The excess material provides physical clearance for the probe 104 such that the enclosure body 110 does not hinder or restrict movement of the probe 104 during operation of the device 102. For example, without the excess material surrounding the probe 104, the enclosure body 110 would impart counteracting pulling forces at the probe 104 against the desired direction of the probe 104, which would slow down or even stop the probe 104 from moving depending on how taut the enclosure body 110 is against the housing 106, which would deleteriously affect the performance of the device 102.

Figure 1G:
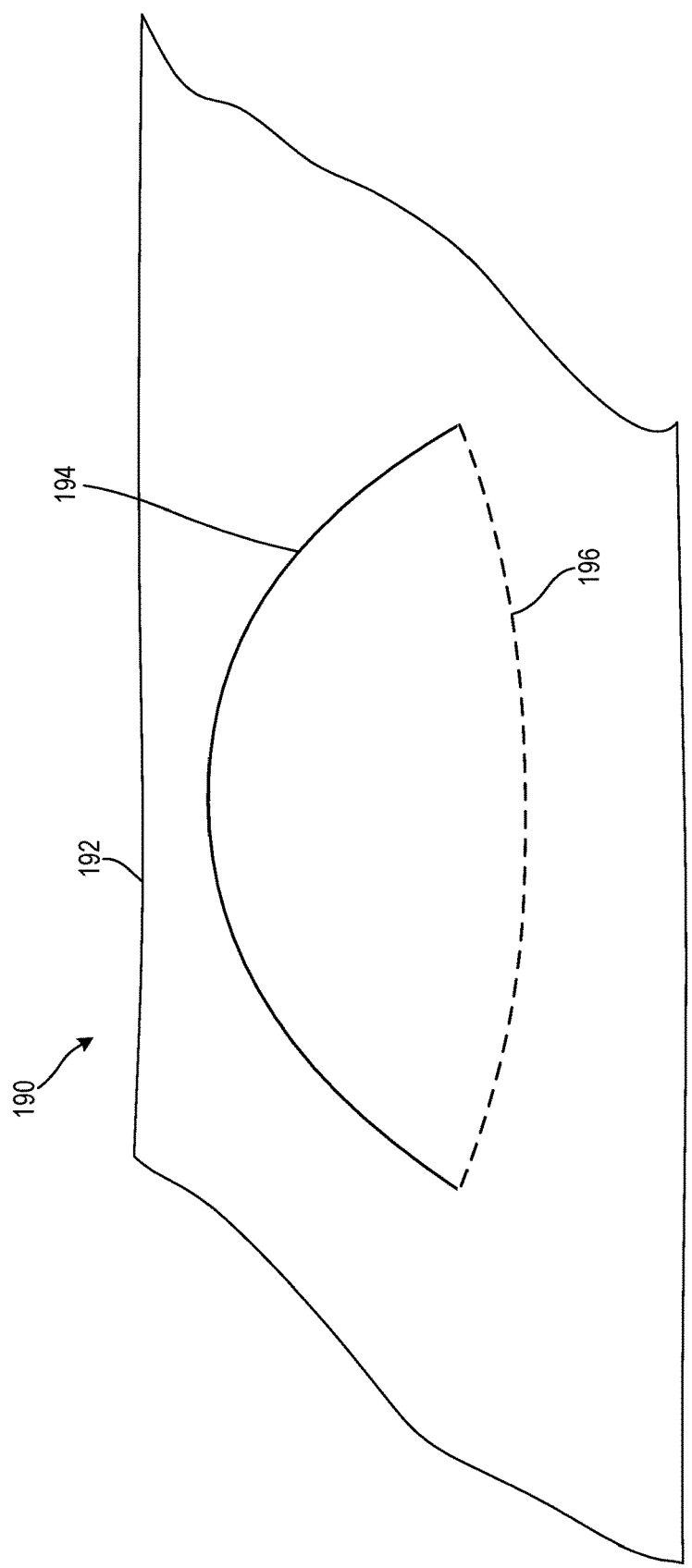
FIG. 1G shows a portion of an enclosure for covering a device including a probe according to various arrangements.

In that regard, FIG. 1G shows a portion 190 of the enclosure body 110 that includes a pocket-like volume according to some arrangements. Other features (e.g., the first hole 120) of the enclosure body 110 are not shown in FIG. 1G for the sake of clarity. The portion 190 may include an excess material 194 which forms the pocket-like volume and an adjacent material 192 that surrounds at least a portion of the excess material 194. In some arrangements, the excess material 194 is joined with the adjacent material 192 at a border connection 196, which may be any suitable attachment mechanism such as but not limited to, adhesives, stitches, welding, and the like. The border connection 196 is liquid-impermeable and particle-impermeable, such that liquid and particles cannot pass through the border connection 196. In other words, the border connection 196 seals any gap between the excess material 194 and the adjacent material 192. In that regard, the excess material 194 and the adjacent material 192 may be separate materials joined together by the border connection 196 during a manufacturing process of the enclosure body 110. In other arrangements, the excess material 194 and the adjacent material 192 are a unitary material and may be formed together during a manufacturing process of the enclosure body 110.

The excess material 194 is configured to form a pocket-like volume such that when the enclosure body 110 covers the housing 106 and when the probe interaction portion engages the probe 104, the excess material 194 is spaced apart from the housing 106, such that a probe-facing surface of the excess material 194 does not contact the housing 106. As shown in FIG. 1G, the excess material 194 (in an expanded, propped up form) may be configured to form the pocket-like volume having an appropiate shape and dimensions to allow the probe 104 to move freely without being hindered by the excess material 194. The excess material 194 may be manufactured to be shaped as the pocket-like volume during a manufacturing process in some arrangements. In other arrangements, the excess material 194 may be made from a stretchable material to be stretched by a user or by the probe 104 when the probe 104 engages the probe interaction portion. For example, as shown in FIG. 1G, the excess material 194 may form a pocket-like volume that has a half-spherical or domed shape. The probe interaction portion ((e.g., the first hole 120 (not shown)) may be located at a peak of the dome of the half-spherical shape or at any other suitable location on the half-spherical shape. One of ordinary skill in art can appreciate that the excess material 194 can also be configured to form a pocket-like volume that has any other suitable shapes such as but not limited to, an oval, a cube, and the like. In that regard, the pocket-like volume may proximate and surround the probe 104. When the enclosure body 110 covers the housing 106, an inner surface of the excess material 194 may be configured to face a front surface of the housing 106, where the front surface defines the cavity 108. The inner surface of the rest of the enclosure body 110 (e.g., other portions of the enclosure body 110 aside from the portion 190) may face or otherwise contact a back surface of the housing 106, where the back surface opposes the front surface.

In some arrangements, the enclosure body 110 includes two or more portions. In some arrangements, the enclosure body 110 includes the excess material 194 and the adjacent material 192, where the adjacent material 192 may include all portions of the enclosure body 110 except the excess material 194. In other arrangements, the enclosure body 110 includes a portion that is configured to proximate or cover the front surface of the housing 106 and another portion that is configured to proximate or cover the back surface of the housing 106. Each portion can be made from a different material. For example, the portion at, surrounding, and/or around the first hole 120 can be made from a relatively thinner and/or more elastic material (e.g., having a higher elasticity characteristic), such that the portion can be stretched for providing the friction fit with the probe 104 in the manner described. The rest of the enclosure body 110 can be made from a thicker and/or less elastic material (e.g., having a lower elasticity characteristic).

In addition or as an alternative to stretching the portion surrounding and around the first hole 120, to allow the first hole 120 to be operatively engaged with the probe 104 to form the seal around the probe 104, the probe interaction portion may include a seal mechanism that is at least one of an elastic band around the first hole 120 (and around the probe 104), a two-piece snap ring in the portion surrounding and around the first hole 120, an adhesive collar on the portion surrounding and around the first hole 120, at least one flap on the portion surrounding and around the first hole 120, at least one strap on the portion surrounding and around the first hole 120, and a co-molded or ultrasound-welded silicone ring around the boundary defined by the first hole 120. The silicone ring may be a collar having a thickness, which increases a surface area along a side surface of the probe 104, providing an improved friction fit as compared to the arrangements in which the excess material 194 may be made from a stretchable material to be stretched by a user or by the probe 104 when the probe 104 engages the probe interaction portion.

In some arrangements, the enclosure body 110 further includes a first marker 170 positioned to indicate (e.g., allowing an operator to recognize) that the first hole 120 is for and corresponds to the probe 104, to facilitate the operator to insert the probe 104 into the first hole 120. In some examples, the first marker 170 is attached to an exterior surface of the enclosure body 110 via adhesives. The exterior surface of the enclosure body 110 is the surface that faces away from the housing 106 when the enclosure 100 is attached, fastened, or otherwise coupled to the housing 106. In some examples, the first marker 170 is attached (e.g., via adhesives), welded, or stitched to an interior surface of the enclosure body 110. The interior surface of the enclosure body 110 is the surface that faces the housing 106 when the enclosure 100 is attached, fastened, or otherwise coupled to the housing 106. The first marker 170 can be printed on the enclosure body 110 (in either the exterior surface or the interior surface) in some examples. Due to biocompatibility concerns, the first marker 170 may be printed on, adhered to, or otherwise attached to the interior surface of the enclosure body 110 (e.g., so that the first marker 170 does not contact a subject).

In some arrangements, the first marker 170 can provide additional rigidity to structurally support the first hole 120. For example, the friction fit or other types of engagement with the probe 104 (in providing the sealing effect) can result in wear and tear to the portion of the enclosure body 110 that surrounds and is around the first hole 120. With the addition of the first marker 170, a portion around the first hole 120 is structurally reinforced by the first marker 170. Therefore, the first marker 170 can be made from a stiffening or rigid material that is more rigid than the material of the portion of the enclosure body 110 that surrounds and is around the first hole 120. On the other hand, the material of the first marker 170 may not be too rigid or sturdy to affect the operations and movements of the probe 104. As such, the first marker 170 may control the stretching of the enclosure body 110 beyond an area of the enclosure body 110 outside of the first marker 170, and may be flexible and lightweight. Furthermore, the thickness of the first marker 170 may be thin enough such that the first marker 170 does not readily peel off from the enclosure body 110 if the first marker 170 is attached to the enclosure body 110 via adhesives. For example, the first marker 170 can be made from a material such as but not limited to, a cardboard material, a plastic material, silicone, and the like.

To structurally support and stabilize the first hole 120, in some examples, the first marker 170 may be adjacent to or abut the first hole 120. In other examples, a distance (e.g., 5 mm, 1 cm, 2 cm, 5 cm, 10 cm, 5 mm-20 cm, and the like) is provided between the first hole 120 and the first marker 170 so as to allow the portion of the enclosure body 110 that surrounds and is around the first hole 120 to stretch to create the friction fit. The distance between the first hole 120 and the first marker 170 is defined as a length of a shortest path between any point on a boundary of the first hole 120 and any point on an inner edge of the first marker 170. The portion of the enclosure body 110 that is between the first marker 170 and the first hole 120 is referred to as an isolated portion of the enclosure body 110, given that the isolated portion is isolated from the rest of the enclosure body 110. While the first marker 170 is shown to be a concentric ring around the first hole 120, one of ordinary skill in the art can appreciate that the first marker 170 can be of any suitable shape (e.g., a triangle, a square, an oval, a rectangle, and the like), size, and position.

Furthermore, the first marker 170 can include a gel reservoir within which a lubricating gel (used to improve acoustic transmission) can be stored. In some arrangements, the gel is ultrasound gel. For example, the material of the first marker 170 can form an interior volume (e.g., the first marker 170 can form a toroid shape) within which the gel can be stored. Given that the first marker 170 is adjacent to or close to the probe 104, the gel can be applied using the gel reservoir of the first marker 170. For example, an operator can pierce the gel reservoir using a sharp object to apply the gel between the head and the probe 104. Given that the volume of the gel reservoir is a known variable, the amount of gel stored in the gel reservoir can be known ahead of time. Thus, the gel reservoir can store an appropriate amount of gel for a given application, controlling the gel application for the operator such that the operator does not need to measure the gel. In some arrangements, one or more dimensions of the first marker 170 (e.g., thickness, width along the enclosure body 110, and so on) can be increased to provide a suitable volume for storing an appropriate amount of gel therein. Accordingly, the first marker 170 as described herein can perform at least three functions: indicating that the first hole 120 is for receiving the probe 104, structurally supporting the first hole 120, and storing gels.

In some arrangements, the first hole 120 may be formed as the probe 104 is being inserted. For example, the portion of the enclosure body 110 corresponding to the first hole 120 may include perforations that can be torn when the probe 104 is pressed against the portion. Areas of the enclosure body 110 around the perforations can be stretched to provide the friction fit in the manner described. If the first marker 170 is used, the first marker 170 can be used to indicate the perforations. The first marker 170 may have a ring shape or may be a circle with perforations such that the perforations of both the first marker 170 and the enclosure body 110 are torn by the probe 104 as the probe 104 is inserted. In some arrangements, the perforations form any suitable pattern for enabling the probe 104 to puncture the enclosure body 110 while maintaining the impermeable seal between the probe 104 and the enclosure body 110.

In some arrangements, the enclosure body 110 includes at least one second hole (e.g., second holes 130 and 135) configured to receive the camera 105, such that the camera 105 protrudes from the at least one second hole when the enclosure 100 covers the housing 106. By providing at least two second holes 130 and 135, improved cost of production and utilization of the enclosure 100 can be realized. For instance, while the device 102 (e.g., shown in FIG. 1F) has the camera 105 on one side of the housing 106, another device (similar to the device 102) positioned opposite to the device 102 in a same headset system may have a camera (similar to the camera 105) on an opposite side of the housing to collect data with respect to another side of subject's head. By providing the two second holes 130 and 135, the same enclosure 100 can be used for any type of device 102 regardless of the position of the camera 105 relative to the housing 106. In that regard, the second hole 130 is configured to receive the camera 105 (positioned at a first position relative to the housing 106), such that the camera 105 protrudes from the second hole 130 when the enclosure 100 is attached to the housing 106. The second hole 135 is configured to receive a camera (positioned at a second position relative to the housing 106 that is different from the first position), such that the camera protrudes from the second hole 135 when the enclosure 100 is attached to the associated housing. Ambidextrous operations as well as mass production can thus be enabled based on a same design.

As described, when the camera 105 registers the subject with respect to the device 102, the camera 105 can extend outward from the housing 106 to avoid the enclosure body 110 being within the field of view (FOV) of the camera 105. As such, the view of the camera 105 is not obstructed or distorted by the enclosure body 110, thus allowing full quality of performance of the camera 105. For example, the camera 105 may be fixed to a mobile platform that can move relative to the housing 106, for example, at least along the X-axis.

In some arrangements, instead of having the at least one second hole (e.g., the second holes 130 and 135), a camera portion of the enclosure body 110 may cover the camera 105 to provide ingress protection to the camera 105. The camera portion of the enclosure body 110 may be made from a particular material to allow the camera 105 to take clear videos and images despite being covered by the portion of the enclosure body 110. The portion (e.g., corners of the enclosure body 110) may be made from a material different from those of other portions of the enclosure body 110. For example, the corners of the enclosure body 110 is made from one of the materials PE, PC, PU, PEI, PVC, and PEEK while other portions of the enclosure body is made from another one of the materials PE, PC, PU, PEI, PVC, and PEEK. As such, the camera portion of the enclosure body 110 configured to cover the camera 105 may be an optically clear window that is rigid, substantially rigid, or flexible. The window may be made from an IR-transmissive material such as but not limited to, polysulfone, PE, polystyrene, and the like. The camera portion of the enclosure body 110 configured to cover the camera 105 may include adhesives configured to attach the camera portion of the enclosure body 110 to the lens of the camera 105. In some arrangements, the adhesives that attach to the camera 105 are configured to allow the camera 105 to take clear images of the subject and may also align with or correspond to the camera portion of the enclosure body 110.

In some arrangements, the enclosure body 110 further includes a second marker (e.g., second markers 140 and 145) positioned to indicate (e.g., allowing an operator to recognize) that a second hole (e.g., the second holes 130 and 135, respectively) is for and corresponds to the camera 105. The second markers 140 and 145 can indicate an orientation (e.g., "LEFT" or "RIGHT") of the camera 105 relative to the housing 106, such that the operator can attach the enclosure 100 to the device 102 in a corresponding and proper orientation (e.g., such that the first hole 120 aligns with the probe 104).

In some examples, each of the second markers 140 and 145 is attached (e.g., via adhesives), welded, or stitched to an exterior surface or an interior surface of the enclosure body 110. Each of the second markers 140 and 145 can be printed on the enclosure body 110 in either the exterior surface or the interior surface in some examples. Due to biocompatibility concerns, each of the second markers 140 and 145 may be printed on, adhered to, or otherwise attached to the interior surface of the enclosure body 110.

In some arrangements, each of the second markers 140 and 145 can provide additional rigidity to structurally support corresponding second holes 130 and 135. Therefore, each of the second markers 140 and 145 can be made from a stiffening or rigid material that is more rigid than the material of the portion of the enclosure body 110 that surrounds and is around the second holes 130 and 135. For example, each of the second markers 140 and 145 can be made from a material such as but not limited to, a cardboard material, a plastic material, silicone, and the like. As such, with the added rigidity provided by the second markers 140 and 145, the enclosure body 110 can be more easily placed and positioned over the camera 105. With the addition of the second markers 140 and 145, portions around the second holes 130 and 135 are structurally reinforced by the second markers 140 and 145.

To structurally support and stabilize the second holes 130 and 135, in some examples, each of the second markers 140 and 145 may be adjacent to or abut a corresponding one of the second holes 130 and 135. In other examples, a distance (e.g., 5 mm, 1 cm, 2 cm, 5 cm, 10 cm, 5 mm-20 cm, and the like) is provided between each of the second markers 140 and 145 and a corresponding one of the second holes 130 and 135. The distance between one of the second holes 130 and 135 and a respective one of the second markers 140 and 145 is defined as a length of a shortest path between any point on a boundary of the one of the second holes 130 and 135 and any point on an inner edge of the respective one of the second markers 140 and 145. While the second markers 140 and 145 are shown to be rectangular, one of ordinary skill in the art can appreciate that the second markers 140 and 145 can be of any suitable shape (e.g., a triangle, a square, an oval, a rectangle, and the like), size, and position.

The enclosure body 110 forms an opening 115 through which the device 102 is placed within an interior volume of the enclosure body 110. A fastening mechanism 150 is provided for attaching, fastening, or otherwise coupling the enclosure 100 to the housing 106 to allow easy installation and removal of the enclosure 100 and to provide secure placement of the enclosure 100 while on the device 102 and while the device 102 is operating. Although the fastening mechanism 150 is shown to be an elastic band configured to be expanded when being placed on the device 102 and tighten around the device 102 once the enclosure 100 is positioned, other examples of the fastening mechanism include, but are not limited to, a hook-and-loop fastener (e.g., Velcro®), adhesive strips, adhesives, buttons, zippers, clamps, and strings. In other arrangements, the opening 115 may not have any fastening mechanism coupled thereto such that the enclosure body 110 simply drapes over the device 102.

In some arrangements, the enclosure body 110 may have a substantially rectangular or square shape. Two pieces of material or a single sheet of material can be joined at edges 160 and 165 via adhesives to form the enclosure 100. In other examples, a zipper, stitching, welding, or another suitable mating mechanism can be provided along the edges 160 and 165 for enclosing and sealing the enclosure body 110 along the edges 160 and 165. In some arrangements, the enclosure 100 is manufactured by, for example, thermoforming, co-molding, or any other suitable manufacturing process. This allows the enclosure 100 to be opened up in two joined sheets of material before use, promoting efficient transportation, manufacturing, and storage. In some arrangements in which the enclosure body 110 is made from two pieces of material joined at the edges 160 and 165, a first piece (a front surface of the enclosure body 110) of the two pieces that includes the first hole 120 may be made from an ultrasound-friendly material (e.g., a material that has an acoustic impedance (Z) that matches or substantially matches a medium such as but not limited to, air through which the ultrasound waves are carried) while a second piece of the two pieces may be made from an ultrasound-unfriendly material (e.g., a material that has an acoustic impedance (Z) that matches less to the medium). Examples of the ultrasound-friendly material include but are not limited to, PE, PC, PU, PEI, PVC, and PEEK having less density. Examples of the ultrasound-unfriendly material include but are not limited to, PE, PC, PU, PEI, PVC, and PEEK having more density. In some arrangements, the ultrasound-friendly material allows ultrasound waves to more easily pass therethrough than the ultrasound-unfriendly material does, or, in other words, the ultrasound-unfriendly material blocks or partially blocks ultrasound waves from passing therethrough while the ultrasound-friendly materially does not.

The first hole 120 may be formed by cutting the corresponding material from the enclosure body 110 (e.g., after or before the enclosure body is formed). The first hole 120 may be at an approximated center of the shape defined by the enclosure body 110. The second holes 130 and 135 may be formed by cutting off the corresponding material from the enclosure body 110 (e.g., efficiently, using a straight cut). As such, the second holes 130 and 135 formed by slits in the enclosure body 110. The fastening mechanism 150 may be placed at an edge of the shape defined by the enclosure body 110, given that the fastening mechanism 150 may be adjacent to or may abut the opening 115. Such configurations have minimal manufacturing cost and allow the enclosure 100 to be mass produced. The shape of the enclosure body 110 allows the enclosures 100 to be stacked together for storage and transportation, thus greatly reducing overhead for storage and transportation. Furthermore, the shape of the enclosure body 110 is selected to reduce the burden on the robotics 103 for moving the probe 104. Thus, one of ordinary skill in the art can appreciate that other shapes and methods to manufacture the enclosure 100 can be likewise implemented in view of the considerations set forth herein.

As referred to here, the probe interaction portion is configured to be operatively engaged with the probe 104 such that the probe 104 is configured to transmit acoustic energy to a subject from within the enclosure 100. In that regard, the probe interaction portion may include one or more of the first hole 120, an area around the first hole 120 that can be stretched to form a friction fit with respect to the probe 104 to provide a seal, another seal mechanism as described, adhesives configured to attach the probe interaction portion of the enclosure 100 to a surface of probe 104 (e.g., in the arrangements in which the first hole 120 is not provided, and the like).

Figure 2A:
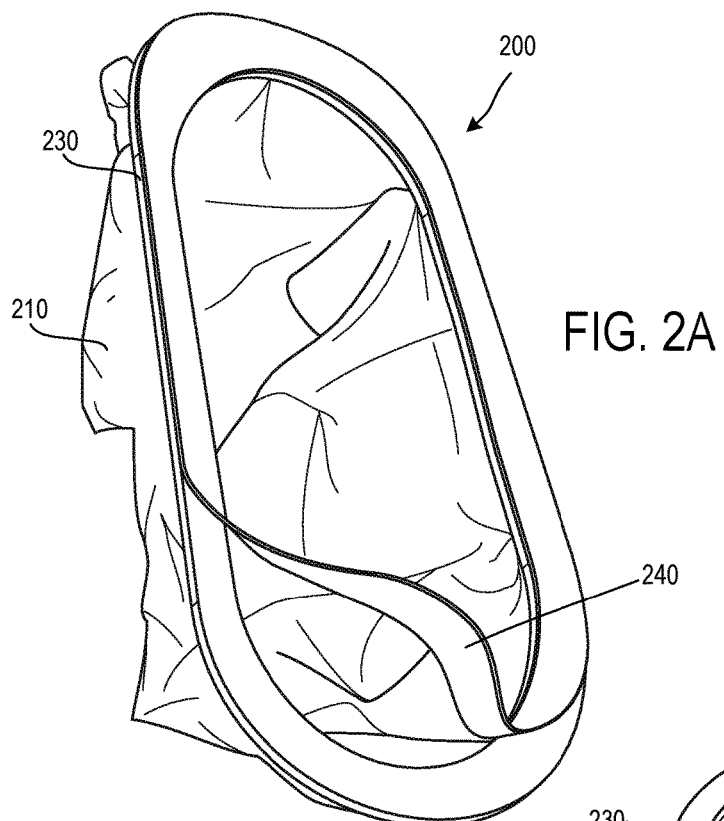
FIG. 2A shows a rear perspective view of an enclosure for covering a device including a probe according to various arrangements.
Figure 2B:
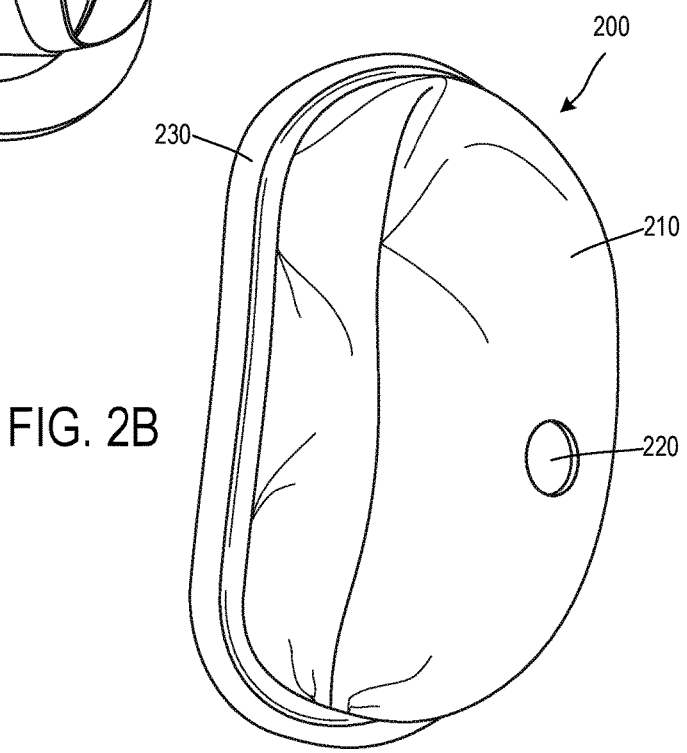
FIG. 2B shows a front perspective view of an enclosure for covering a device including a probe according to various arrangements.
Figure 2C:
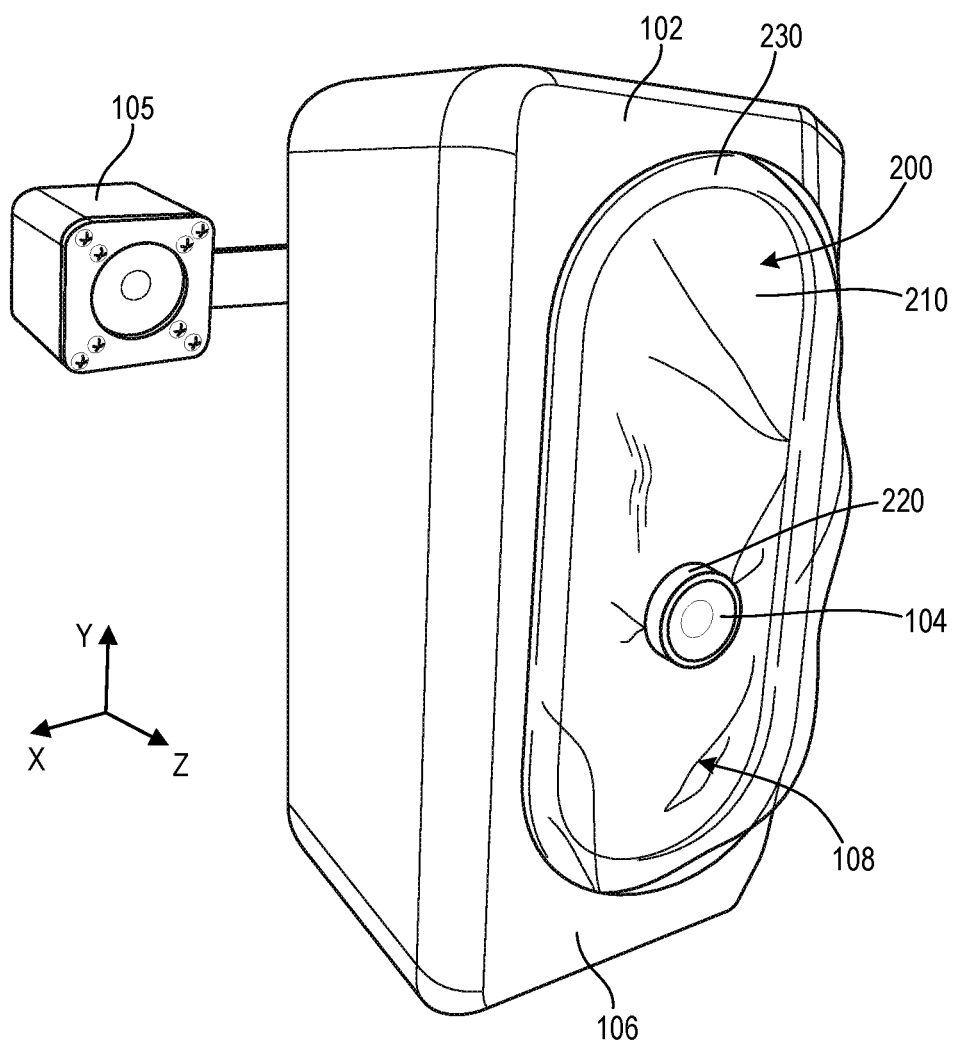
FIG. 2C shows a perspective view of an enclosure covering a device including a probe according to various arrangements.

FIGS. 2A-2C show another enclosure 200 for covering the device 102 according to various arrangements. Referring to FIGS. 1A-2C, the enclosure 200 includes an enclosure body 210 configured to cover the cavity 108 when the enclosure 200 is attached, fastened, or otherwise coupled to the housing 106.

A base 230 is configured to attach, fasten, or otherwise couple the enclosure body 210 to the housing 106. In some arrangements, the perimeter of the base 230 may approximate or correspond to (e.g., be slightly greater than) a perimeter of the cavity 108 and can be attached to a boundary defined by the housing 106 surrounding the cavity 108, such that the base 230 surrounds the cavity 108 when the base 230 is removably secured to the housing 106. For example, given that the cavity 108 as shown has an oval shape (as shown in FIGS. 2A-2C), the base 230 may also have a corresponding oval shape. The base 230 can correspond to another suitable shape of the cavity 108. The dimensions of the base 230 exceed the dimensions of the cavity 108 such that the enclosure 200 can be attached to an exterior surface of the housing 106 surrounding the cavity 108. Thus, as compared to the enclosure 100, the enclosure 200 can be manufactured with less material because the enclosure 200 does not cover a substantial portion or an entirety of the housing 106. Furthermore, the enclosure 200 is configured to be placed away from the camera 105 and outside of the FOV of the camera 105.

The base 230 may structurally support the enclosure body 210. In that regard, the base 230 may be rigid (e.g., may be more rigid than the enclosure body 210) to provide a foundation to hold the enclosure body 210 in place with respect to the housing 106. For example, the base 230 may be made from, for example, thermoplastic polyurethane (TPU) with a thin form ring. Other suitable materials for the base 230 can also be used. For example, the base 230 may be made from a foam material (e.g., expanded foam, compression molded foam, or the like) that provides ingress protection. The base 230 includes a removable portion 240 that can be removed to expose adhesives. Thus, an operator can simply peel off the removable portion 240 to attach the enclosure 200 to the housing 106 to form a seal between the base 230 and the housing 106. Other mechanisms (e.g., a snap fit, screws, and the like) for attaching the base 230 to the housing 106 can be likewise implemented as long as a seal can be created between the base 230 and the housing 106. In some arrangements, the seal formed between the base 230 and the housing 106 is tight enough to prevent liquid or particles from entering into the cavity 108.

The enclosure body 210 is made of a material that provides ingress protection against liquid (e.g., blood, sweat, and water) and particles (e.g., dust and hair) for the cavity 108, similar to the enclosure body 110. Furthermore, in some arrangements, the enclosure body 210 is made of a biocompatible material suitable for contacting a human body (e.g., the head of the subject) similar to the enclosure body 110. Moreover, in some arrangements, the enclosure body 210 is made of a lightweight material or an ultra-lightweight material similar to the enclosure body 110, to impose less stress on the robotics 103 when the probe 104 is moved.

Therefore, in considering ingress protection, elasticity, biocompatibility, and weight, the enclosure body 210 can be made from a material such as but not limited to, PE, PC, PU, PEI, PVC, and PEEK in some examples. In other examples, the enclosure body 210 can be made from a layer of thin silicone, biocompatible waterproof fibers or fabric, a medical curtain (e.g., a PE curtain), treated paper, Tyvek®, and the like. In some arrangements, the enclosure 200 can be manufactured by first providing a mold defining a shape of the enclosure body 210 (e.g., a recess within the mold configured to shape the bulge of the enclosure body 210) and pressing the material of the enclosure body 210 within the mold.

As shown in FIGS. 2A-2C, the enclosure body 210 may bulge outward from the cavity 108 such that a substantial portion (e.g., greater than 50%) or all of the enclosure body 210 is outside of the cavity 108. Such arrangements can reduce the probability that the enclosure body 210 is caught by the robotics 103 while the robotics 103 are operational. Alternatively, a substantial portion (e.g., greater than 50%) or all of the enclosure body 210 may bulge inward into the cavity 108 to reduce the probability that the enclsoure body 210 contacts a subject while the probe 104 is operational and is proximate to or contacts the subject. The material of the enclosure body 210 may be sufficiently plentiful (e.g., to form the bulge as described) such that the movement of the probe 104 is not restricted (e.g., the probe 104 is free to move to any edge of the cavity 108 without being restricted by the material of the enclosure body 210).

The outward bulging of the enclosure body 210 forms a pocket-like volume according to some arrangements. For example, the enclosure body 210 may correspond to an excess material which forms the pocket-like volume such that when the enclosure body 210 is attached to the housing 106 and when the probe interaction portion engages the probe 104, the excess material (e.g., the enclosure body 210) is spaced apart from the housing 106, such that a probe-facing surface of the excess material does not contact the housing 106. The excess material (in an expanded, propped-up form) may be configured to form the pocket-like volume having an appropriate shape and dimensions to allow the probe 104 to move freely without be hindered by the excess material. The excess material may be manufactured to be shaped as the pocket-like volume during a manufacturing process in some arrangments. In other arrangements, the excess material may be made from a stretchable material to be stretched by a user or by the probe 104 when the probe 104 engages the probe interaction portion. For example, the excess material may form a pocket-like volume that has a substantially half-spherical or domed shape, including a side wall extending from the base 230. The probe interaction portion (e.g., the first hole 220) may be located at a peak of the dome of the substantially half-spherical shape or at any other suitable location on the substantially half-spherical shape. One of ordinary skill in art can appreciate that the excess material can also be configured to form a pocket-like volume that has any other suitable shapes such as but not limited to, an oval, a cube, and the like. In that regard, the pocket-like volume may proximate and surround the probe 104. As referred to here, the probe interaction portion is configured to be operatively engaged with the probe 104 such that the probe 104 is configured to transmit acoustic energy to a subject from within the enclosure 200. In that regard, the probe interaction portion may include one or more of the first hole 220, an area around the first hole 220 that can be stretched to form a friction fit with respect to the probe 104 to provide a seal, another seal mechanism as described, adhesives configured to attach the probe interaction portion to a surface of the probe 104 (e.g., in the arrangements in which the first hole 220 is not provided, and the like).

The enclosure 200 (e.g., the enclosure body 210) defines a first hole 220. The first hole 220 is configured to be operatively engaged with the probe 104, exposing a portion of the probe 104. The first hole 220 may be similar to the first hole 120. In some arrangements, the first hole 220 forms a seal around the probe 104 when the enclosure 200 is attached, fastened, or otherwise coupled to the housing 106, similar to the first hole 120. That is, a portion of the enclosure body 210 surrounding the first hole 220 forms a friction-fit seal around the probe 104 by stretching that portion when the probe 104 is inserted through the first hole 220.

In some arrangements, when the enclosure 200 is attached, fastened, or otherwise coupled to the housing 106, the portion surrounding and around the first hole 220 corresponds to extra or excess material of the enclosure body 210. As shown, the excess material forms a pocket-like volume to allow the portion surrounding and around the first hole 220 to move freely with the probe 104 when the enclosure 200 is attached, fastened, or otherwise coupled to the housing 106. The excess material of the enclosure 200 may be similar to that of the enclosure 100 as described above.

In some arrangements, the enclosure body 210 includes two or more portions. Each portion can be made from a different material. For example, the portion surrounding and around the first hole 220 can be made from a thinner and/or relatively more elastic material (e.g., having a higher elasticity characteristic), such that the portion can be stretched for provide the friction fit with the probe 104 in the manner described. The rest of the enclosure body 210 can be made from a thicker and/or less elastic material (e.g., having a lower elasticity characteristic). On the other hand, given that the enclosure body 210 covers the cavity 108, the entire enclosure body 210 may be made from a same elastic material.

In addition or as an alternative to stretching the portion surrounding and around the first hole 220, to allow the first hole 220 to be operatively engaged with the probe 104 to form the seal around the probe 104, the probe interaction portion may include a seal mechanism that is at least one of an elastic band around the first hole 220 (and around the probe 104), a two-piece snap ring in the portion surrounding and around the first hole 220, an adhesive collar on the portion surrounding and around the first hole 220, at least one flap on the portion surrounding and around the first hole 120, at least one strap on the portion surrounding and around the first hole 220, and a co-molded or ultrasound welded silicone ring around the boundary defined by the first hole 220. The silicone ring may be a collar having a significant thickness, which increases a surface area along a side surface of the probe 104, providing an improved friction fit.

In some arrangements, the enclosure body 210 further includes a marker (not shown) such as but not limited to, the first marker 170 can be used to indicate (e.g., allowing an operator to recognize) that the first hole 220 is for receiving the probe 104, to structurally support the first hole 220, and to store gels in the manner described. Perforations can be provided to the enclosure body 110 (and the marker, if desired) to form the first hole 220 when the probe 104 is pressed against an area of the enclosure body 210 corresponding to the first hole 220 in the manner described.

Figure 3:
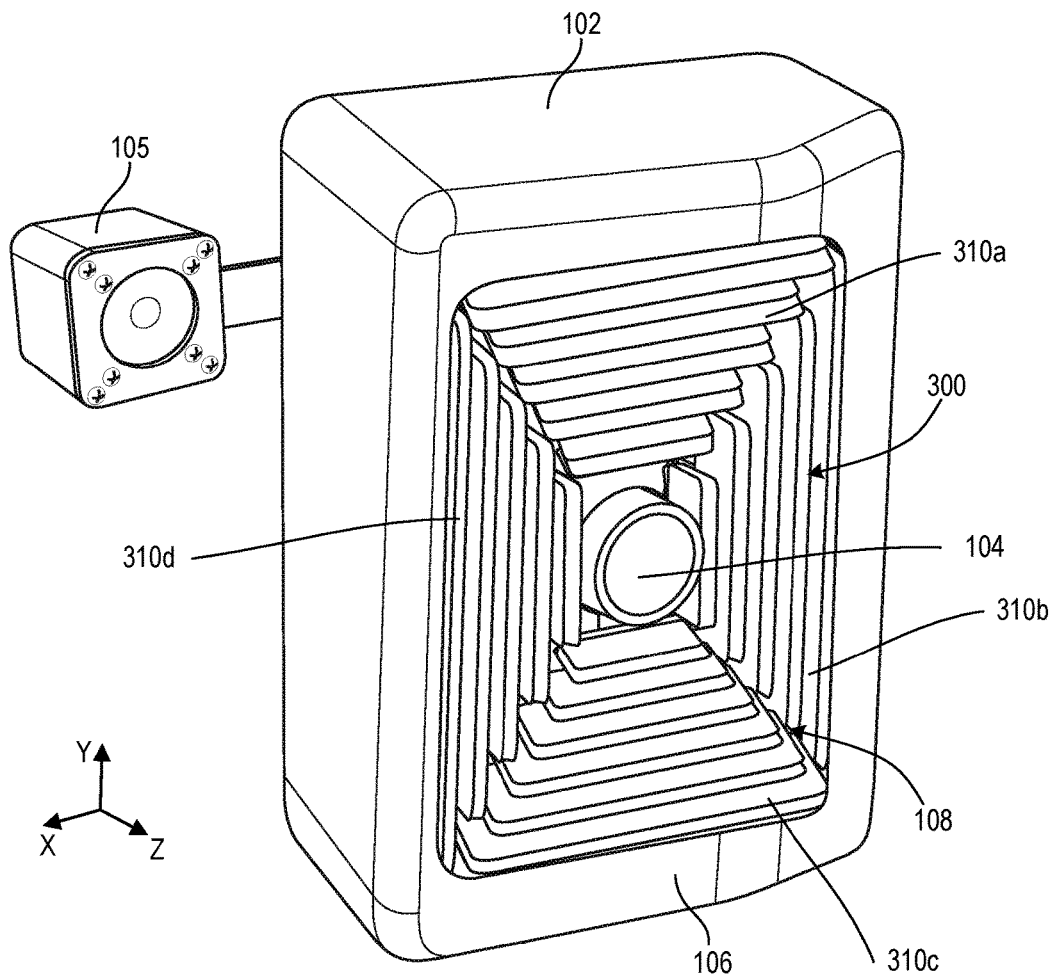
FIG. 3 shows a perspective view of an enclosure covering a device including a probe according to various arrangements.

FIG. 3 shows a perspective view of an enclosure 300 covering the device 102 according to various arrangements. Referring to FIGS. 1A-3, the enclosure 300 may be a permanently-fixed enclosure that seals the cavity 108 in its entirety to provide ingress protection. The enclosure 300 includes ridged portions 310a-310d. The enclosure 300 (e.g., the ridged portions 310a-310d) is permanently fixed to (via mechanical mating) the probe 104 and sides of the cavity 108 via welding, adhesive, one or more hooks/latches, one or more separate screws, press fittings, or the like. The enclosure 300 may be made from a material such as but not limited to, PE, PE, PC, PU, PEI, PVC, and PEEK in some examples. In other examples, the enclosure 300 can be made from a layer of thin silicone, biocompatible waterproof fibers or fabric, a medical curtain (e.g., a PE curtain), paper (e.g., treated paper), Tyvek®, leather (e.g., synthetic or genuine leather), hard plastic, cardboard, metal, and the like. In some arrangements, the enclosure 300 may be made from silicone and may be co-molded or welded to a portion of the probe 104 and sides of the cavity 108. The material of the enclosure 300 may be selected based on a consideration that the material is capable of expansion and contraction of the enclosure 300 in the manner described.

Each of the ridged portions 310a-310d includes folds, pleats, or ridges to allow extension or contraction along at least one axis (e.g., similar to the movement of bellows of an accordion instrument), as the ridged portions 310a-310d are configured to move with the probe 104. For example, as the probe 104 moves in a direction having a component along the X-axis (e.g., an axis along a length of the cavity 108 from the top to the bottom of the housing 106), one of the portions 310a and 310c expands (e.g., the ridges or pleats of the portion elongates or become further away from adjacent ridges or pleats) while the other one of the portions 310a and 310c contracts (e.g., the ridges or pleats of the portion shrink or become closer to adjacent ridges or pleats).

Furthermore, as the probe 104 moves in a direction having a component along the Y-axis, one of the portions 310b and 310d expands while the other one of the portions 310b and 310d contracts. As the probe 104 moves in a direction having a component along the Z-axis, all portions 310a-310d expand or contract together. Accordingly, in some arrangements, each of the ridged portions 310a-310b expands or contracts depending on the position and movement of the probe 104 such that the probe 104 has freedom of movement in all directions without resistance from the enclosure 300.

Figure 4:
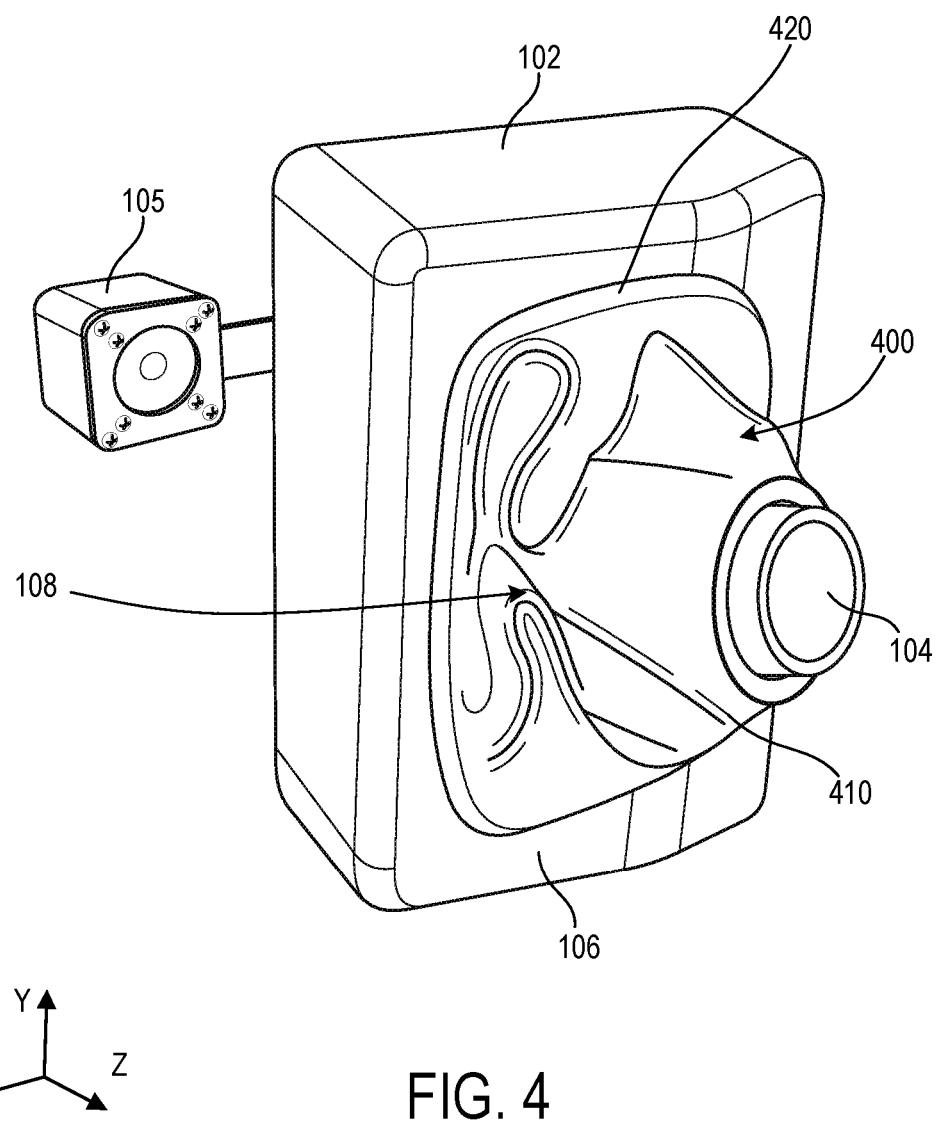
FIG. 4 shows a perspective view of an enclosure covering a device including a probe according to various arrangements.

FIG. 4 shows a perspective view of an enclosure 400 covering the device 102 according to various arrangements. Referring to FIGS. 1A-4, the enclosure 400 may be a permanently-fixed enclosure that seals the cavity 108 in its entirety to provide ingress protection. The enclosure 400 includes an enclosure body 410, which is similar to a baffle. The enclosure 400 is permanently fixed (via mechanical mating) to the probe 104 and sides of the cavity 108 via a welding, adhesive, one or more hooks/latches, one or more separate screws, press fittings, or the like. The enclosure 400 may be made from a material such as but not limited to, PE, PE, PC, PU, PEI, PVC, and PEEK in some examples. In other examples, the enclosure 400 can be made from a layer of thin silicone, biocompatible waterproof fibers or fabric, a medical curtain (e.g., a PE curtain), treated paper, Tyvek®, leather and the like. In some arrangements, the enclosure 400 may be made from silicone and may be co-molded or welded to a portion of the probe 104 and sides of the cavity 108. The material of the enclosure 400 may be selected based on a consideration that the material has high tolerance to expansion and contraction of the enclosure 400 in the manner described. The enclosure 400 has excess material that forms a pocket-like volume to allow the enclosure 400 to move freely with the probe 104, which extends from the enclosure 400, in any suitable direction in the X, Y, and Z-axes.

Figure 5:
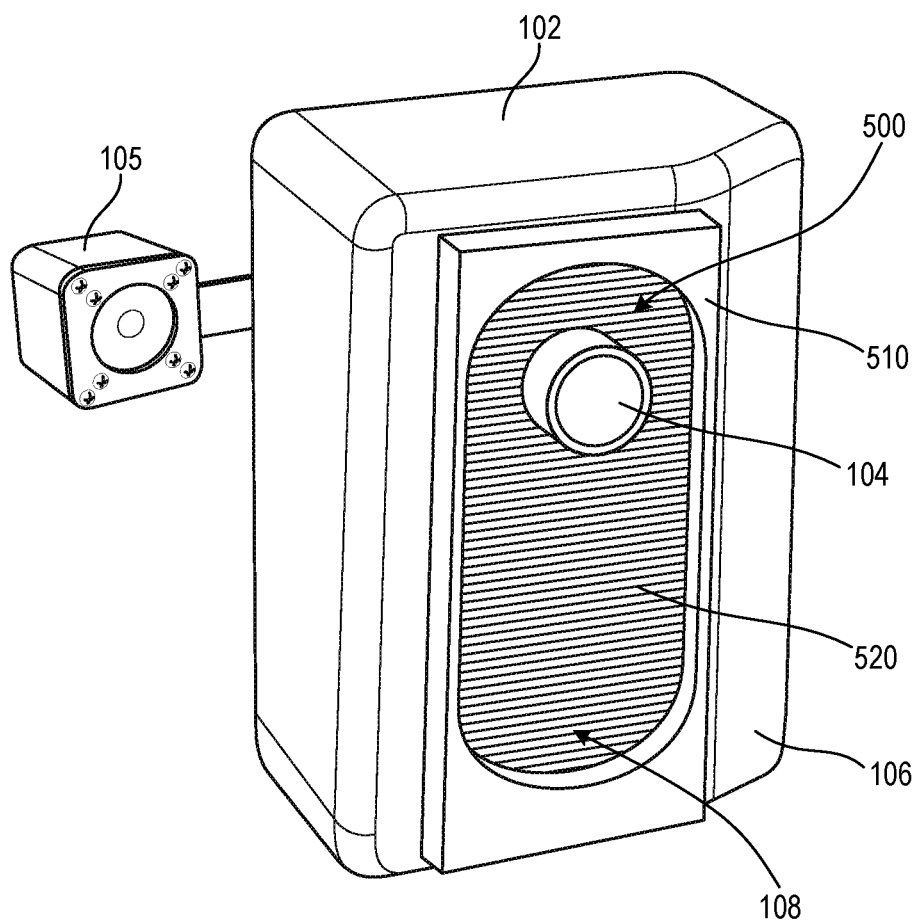
FIG. 5 shows a perspective view of an enclosure covering a device including a probe according to various arrangements.
Figure 5:
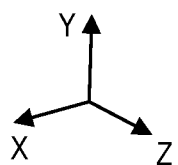

FIG. 5 shows a perspective view of an enclosure 500 covering the device 102 according to various arrangements. Referring to FIGS. 1A-5, the enclosure 500 may be a permanently-fixed enclosure that seals the cavity 108 in its entirety to provide ingress protection. The enclosure 500 includes a base 510 that is fixed (via mechanical mating) to the sides of the cavity 108 via welding, adhesive, one or more hooks/latches, one or more separate screws, press fittings, or the like. The enclosure 500 includes an enclosure body 520 having individual pieces being movably joined together similar to a garage door. Each piece of the enclosure body 520 may be made from a material such as but not limited to, PE, PE, PC, PU, PEI, PVC, and PEEK in some examples. In other examples, each piece of the enclosure body 520 can be made from a layer of silicone, biocompatible waterproof fibers or fabric, a medical curtain (e.g., a PE curtain), treated paper, Tyvek®, leather and the like. The material of the pieces may be selected based on a consideration that the material has high tolerance to the mechanical movement of the enclosure 500 in the manner described. A portion of the enclosure body 520 (e.g., some of the pieces) may form a circle and may be permanently fixed to the probe 104 via welding, adhesive, one or more hooks/latches, one or more separate screws, press fittings, or the like. At least one first motor is configured to move the enclosure body 520 along the X-axis. At least one second motor is configured to move the enclosure body 520 along the Y-axis. Pieces moved beyond the boundary defined by the cavity may be folded together to conserve space.

Figure 6A:
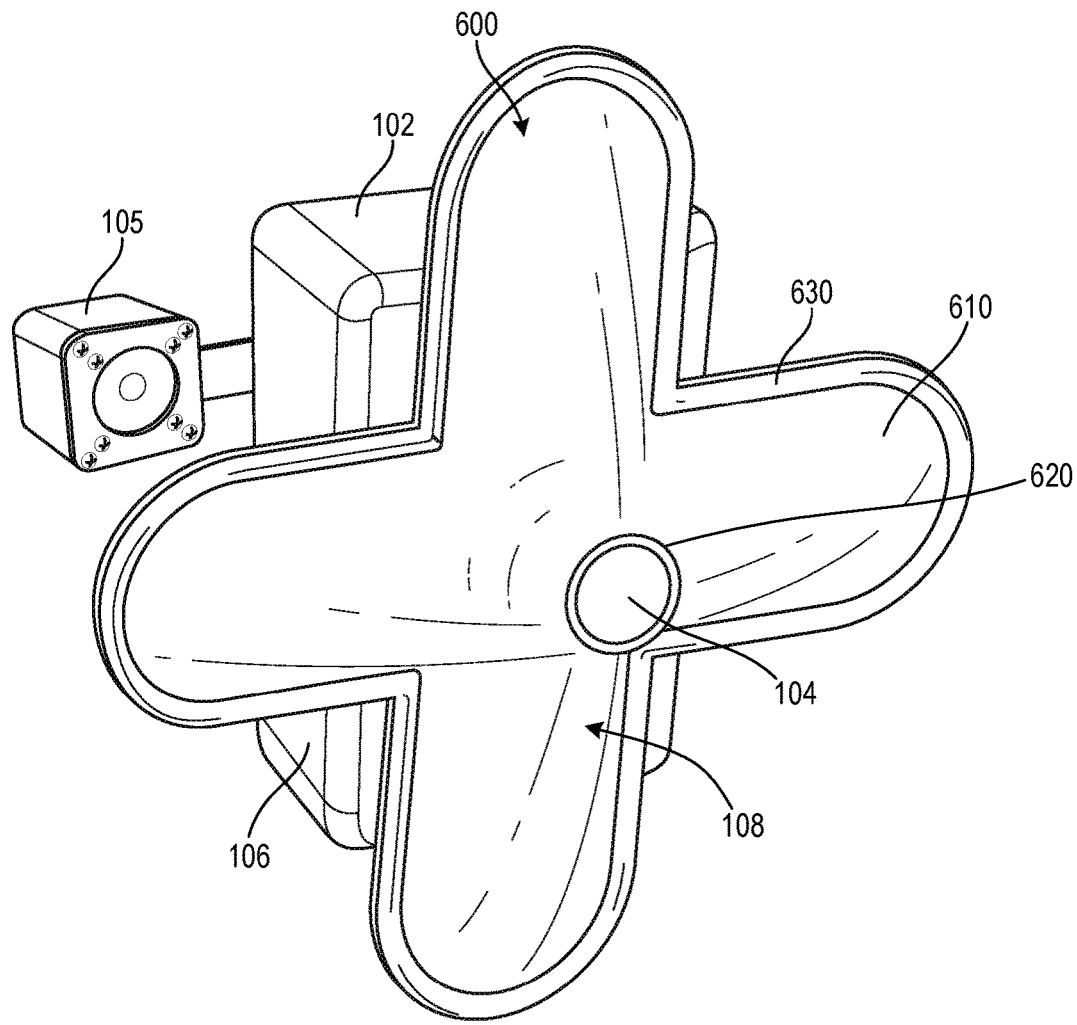
FIG. 6A shows a perspective view of an enclosure configured to cover a device including a probe according to various arrangements.
Figure 6B:
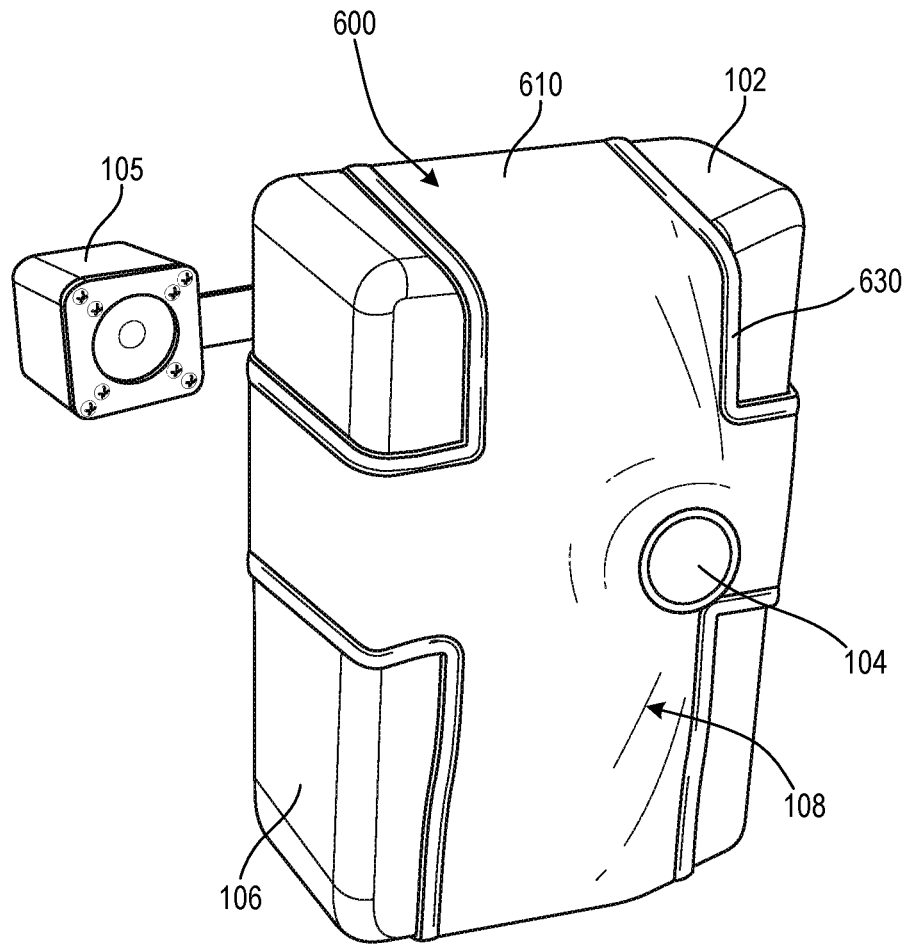
FIG. 6B shows a perspective view of an enclosure covering a device including a probe according to various arrangements.
Figure 6B:
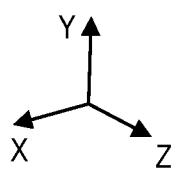

FIG. 6A shows a perspective view of an enclosure 600 configured to cover the device 102 according to various arrangements. FIG. 6B shows a perspective view of the enclosure 600 covering the device 102 according to various arrangements. Referring to FIGS. 1A-6B, the enclosure 600 has an enclosure body 610 shaped to have one or more tabs. While 4 tabs are shown, one of ordinary skill in the art can appreciate that more or less of a number of tabs can be provided. A base 630 is provided along an edge of the enclosure body 610 (along an edge of the tabs) to attach the enclosure body 610 to the housing 106. The base 630 may include adhesives or another suitable mechanism such as a hook-and-loop fastener (e.g., Velcro®) for attaching the enclosure body 610 to cover the cavity 108. An operator can wrap the tabs of the enclosure body 610 around the housing 106 and attach the base 630 to the housing 106 by applying pressure to the base 630 to form a seal via the adhesives.

The enclosure body 610 may have a hole 620 (such as but not limited to, the holes 120 and 220) for receiving the probe 104 and forming a seal with respect to the probe 104. A marker such as but not limited to, the marker 170 may be provided to indicate that the hole 620 is for receiving the probe 104, to structurally support the hole 620, and to store gels in the manner described. Perforations can be provided to the enclosure body 610 (and the marker, if desired) to form the hole 620 when the probe 104 is pressed against an area of the enclosure body 610 corresponding to the hole 620 in the manner described.

Alternatively, in some arrangements, the enclosure body 610 does not have a hole (e.g., the hole 620) through which the probe 104 protrudes. Instead, the enclosure body 610 includes a probe contact portion (not shown). The probe contact portion is configured to contact and move with the probe 104 when the enclosure 600 is attached to or covers the housing 106. For example, the probe contact portion may be at an interior surface of the enclosure body 610 and includes adhesives for releasably attaching the enclosure 600 to the probe 104. In some arrangements, the probe contact portion does not include any adhesives for attaching the enclosure 600 (e.g., the probe contact portion) to the probe 104. Instead, the enclosure 600 (e.g., the probe contact portion) is configured to be stuck and remain in contact with (or attracted to) the probe 104 via a static charge force. For instance, an operator may rub a subject-facing surface of the probe contact portion when the enclosure 600 encloses at least a portion of the housing 106 to create static charges on the probe contact portion, such that a probe-facing surface (on the other side of the subject-facing surface) of the probe contact portion is attracted to the probe 104. In other arrangements, the probe-facing surface of the probe contact portion contacts the probe 104 while a string or band (e.g., an elastic band such as but not limited to a rubber band) is strung around the probe 104 and the probe contact portion to secure the probe contact portion to the probe 104. The probe contact portion may be shaped to take into account the concave shape of the probe 104. The probe contact portion may be configured such that no gap (e.g., air gap) exists between the surface of the probe 104 and the enclosure body 610.

The enclosure body 610 may be made from a material such as but not limited to, PE, PE, PC, PU, PEI, PVC, and PEEK in some examples. In other examples, the enclosure body 610 can be made from a layer of thin silicone, biocompatible waterproof fibers or fabric, a medical curtain (e.g., a PE curtain), treated paper, Tyvek®, leather and the like. The enclosure body 610 has excess material that forms a pocket-like volume (e.g., when attached to the housing 106) to allow the enclosure body 610 to move freely with the probe 104 in any suitable direction in the X, Y, and Z-axes. For example, the enclosure body 610 can include a portion such as but not limited to, the portion 190 as shown in FIG. 1G for provisioning the pocket-like volume as described.

Figure 7:
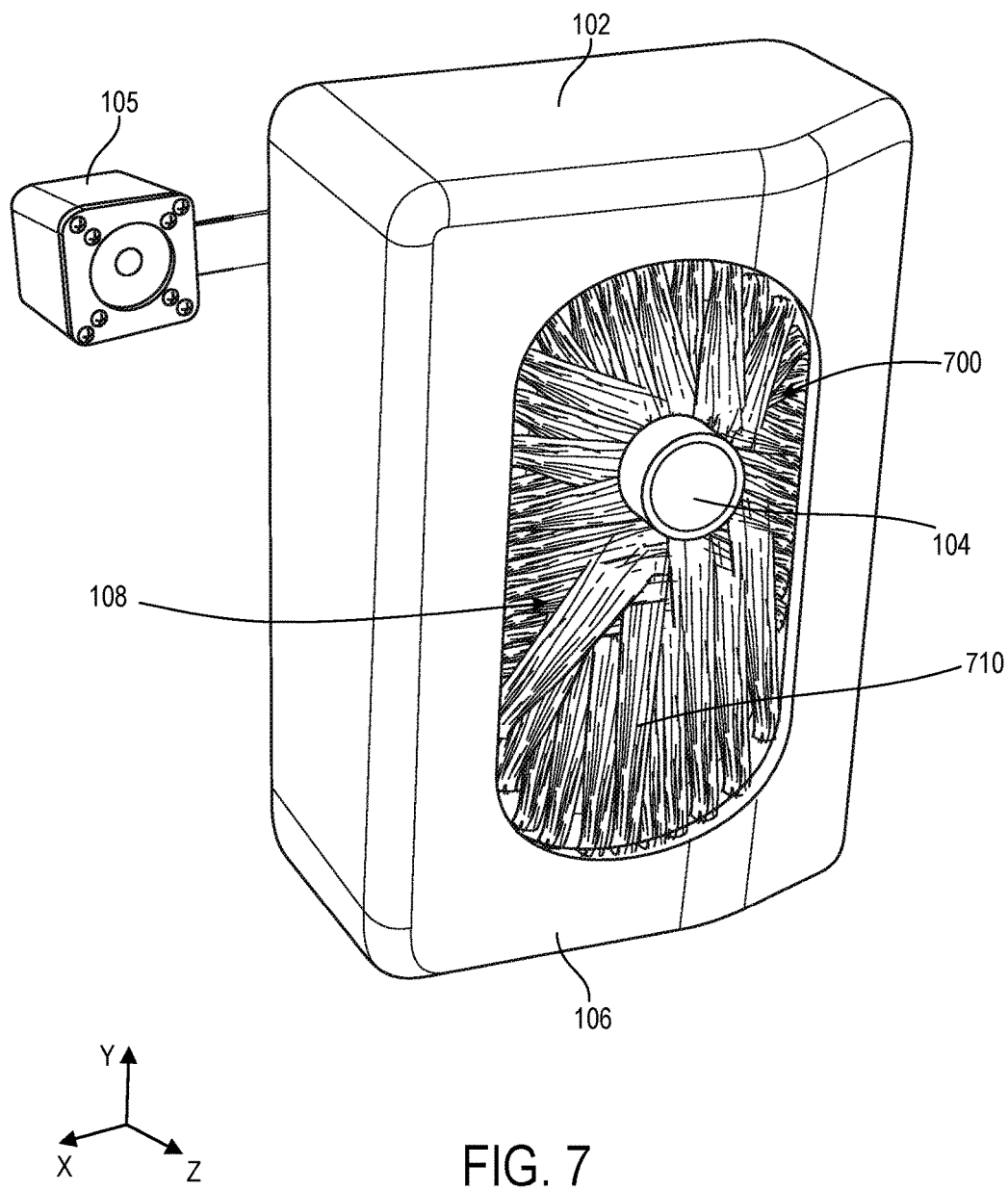
FIG. 7 shows a perspective view of an enclosure covering a device including a probe according to various arrangements.

FIG. 7 shows a perspective view of an enclosure 700 covering the device 102 according to various arrangements. Referring to FIGS. 1A-7, the enclosure 700 may be a permanently fixed enclosure that seals the cavity 108 in its entirety to provide ingress protection. The enclosure 700 includes an enclosure body 710 having bristles. The bristles are fixed (via mechanical mating) to sides of the cavity 108 via welding, adhesive, one or more hooks/latches, one or more separate screws, press fittings, or the like. The bristles may be made from a material such as but not limited to, PE, PE, PC, PU, PEI, PVC, and PEEK in some examples. In other examples, the bristles may be made from a material such as but not limited to, animal (e.g., horse) hair, metal, or metal alloy. The bristles may form a comb-like structure. As the probe 104 is moved in any suitable direction in the X, and Y-axes, some of the bristles may curl while other bristles may be uncurled or partially uncurled. The bristles may have a density sufficient to provide ingress protection against liquid and particles. The bristles further have sufficient length to assure that even as the probe 104 is moved to an edge or corner of the cavity 108, the bristles can contact the probe 104 for form a seal. In some arrangements, the bristles extend from the edges of the cavity towards the center of the cavity (e.g., towards the probe 104).

Figure 8A:
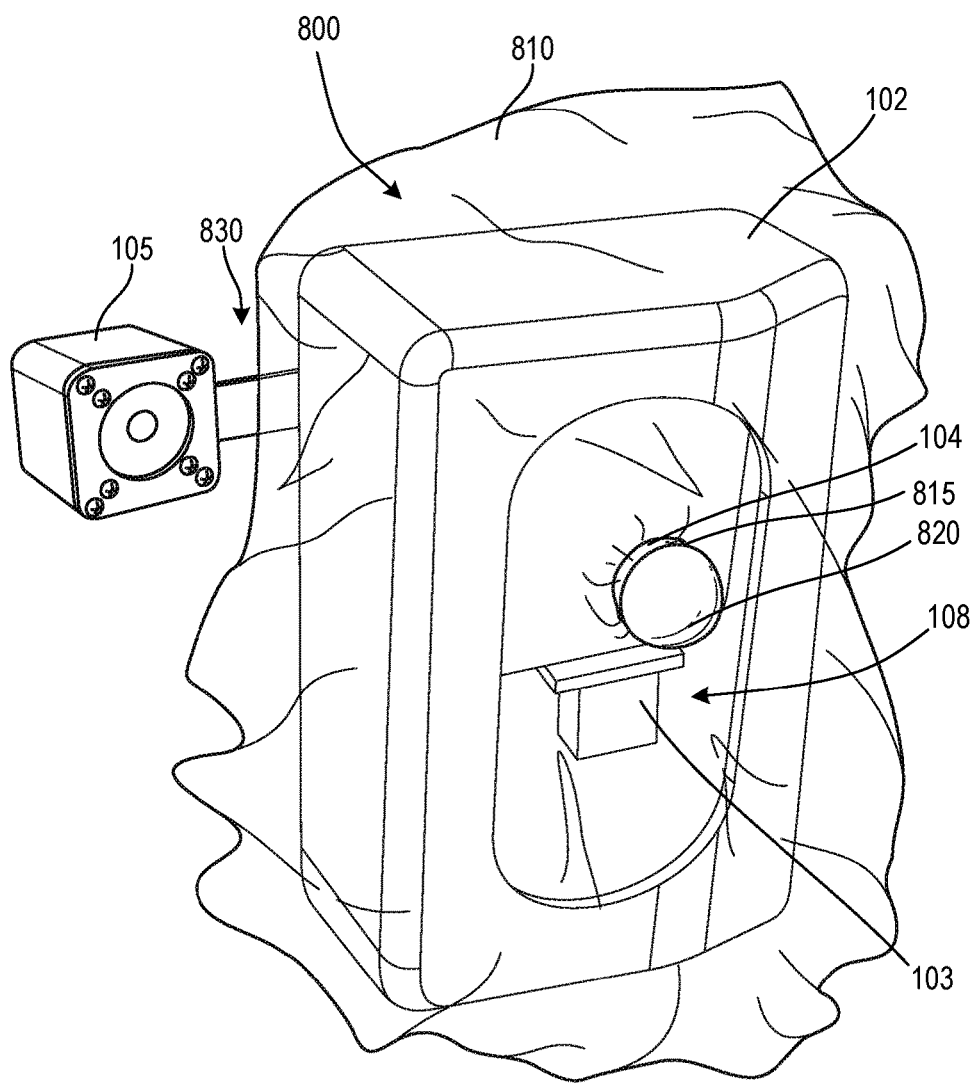
FIG. 8A shows a perspective view of an enclosure covering a device including a probe according to various arrangements.

FIG. 8A shows a perspective view of an enclosure 800 covering the device 102 according to various arrangements. Referring to FIGS. 1A-8A, the enclosure 800 may be similar to the enclosure 100, with certain distinctions. For example, the enclosure 800 may include an enclosure body 810 such as but not limited to, the enclosure body 110 to provide ingress protection against liquid and particles for the cavity 108. The enclosure body 810 may include excess material around the probe 104 that form a pocket-like volume to reduce burden or resistance on the robotics 103 as the robotics 103 move the probe 104. The enclosure 800 may include at least one hole 830 for receiving the camera 105 such as but not limited to, the second holes 130 and 135. Furthermore, the enclosure 800 may include an opening (not shown) and a fastening mechanism (not shown), such as but not limited to, the opening 115 and the fastening mechanism 150, respectively. Still further, the enclosure 800 may include markers such as but not limited to, the markers 140 and 170.

The enclosure 800 differs from the enclosure 100 in that the enclosure body 810 does not have a hole (e.g., the first hole 120) through which the probe 104 protrudes. Instead, the enclosure body 810 includes a probe contact portion 815. The probe contact portion 815 is configured to contact and move with the probe 104 when the enclosure 800 is attached to or covers the housing 106. For example, the probe contact portion 815 may be at an interior surface of the enclosure body 810, and includes adhesives for attaching the enclosure 800 (e.g., the probe contact portion 815) to the probe 104. In some arrangements, the probe contact portion 815 does not include any adhesives for attaching the enclosure 800 (e.g., the probe contact portion 815) to the probe 104. Instead, for example, the enclosure 800 (e.g., the probe contact portion 815) is configured to be stuck and attracted to the probe 104 via a static charge force. For instance, an operator may rub a subject-facing surface of the probe contact portion 815 when the enclosure 800 encloses at least a portion of the housing 106 to create static charges on the probe contact portion 815, such that a probe-facing surface (on the other side of the subject-facing surface) of the probe contact portion 815 is attracted to the probe 104. In other arrangements, the probe-facing surface of the probe contact portion 815 contacts the probe 104 while a string or band (e.g., an elastic band such as but not limited to a rubber band) is strung around the probe 104 and the probe contact portion 815 to secure the probe contact portion 815 to the probe 104. The probe contact portion 815 may be shaped to take into account the concave shape of the probe 104. The probe contact portion 815 may be configured such that no gap (e.g., air gap) exists between the surface of the probe 104 and the enclosure body 810.

In some arrangements, the enclosure 800 includes the standoff member 820 on the exterior surface of the enclosure body 810. The enclosure body 810 and the standoff member 820 are formed as a unitary structure, or the standoff member 820 is permanently or removably attached to the enclosure body 810 via adhesives, a hook-and-loop fastener (e.g., Velcro®), or the like. In some arrangements, the enclosure body 810 and the standoff member 820 are formed with a same material. In other arrangements, a material of the enclosure body 810 and a material of the standoff member 820 are different. The probe contact portion 815 is between the standoff member 820 and the probe 104.

The standoff member 820 is configured to contact a subject (e.g., a head of the subject). Touching the probe 104 directly against the subject's head accelerates wear and tear on the device 102 and makes the subject uncomfortable. Thus, the standoff member 820 can be permanently fixed or removably attached to the enclosure body 810 to serve as a buffer. An end of the standoff member 820 close to the probe 104 may conform to the concave shape of the probe 104 to ensure that there is no air gap between the standoff member 820 and the probe 104 (the probe contact portion 815). The other, opposite end of the standoff member 820 may be substantially flat or conform to a shape of a part of the head that the standoff member 820 is configured to contact, to provide additional comfort to the subject.

In some arrangements, the standoff member 820 is made from a material such as but not limited to, PE, PE, PC, PU, PEI, PVC, and PEEK in some examples. In other examples, the enclosure body 810 can be made from a layer of thin silicone, biocompatible waterproof fibers or fabric, a medical curtain (e.g., a PE curtain), treated paper, Tyvek®, foam, sponge, and the like. In some arrangements, the standoff member 820 may be filled with the material of the enclosure body 810, air, or an ultrasound transmissive material. In other arrangements, the standoff member 820 may store gel. The gel can be applied using the gel reservoir of the standoff member 820. For example, an operator can pierce the standoff member 820 using a sharp object to apply the gel between the head and the probe 104.

Figure 8B:
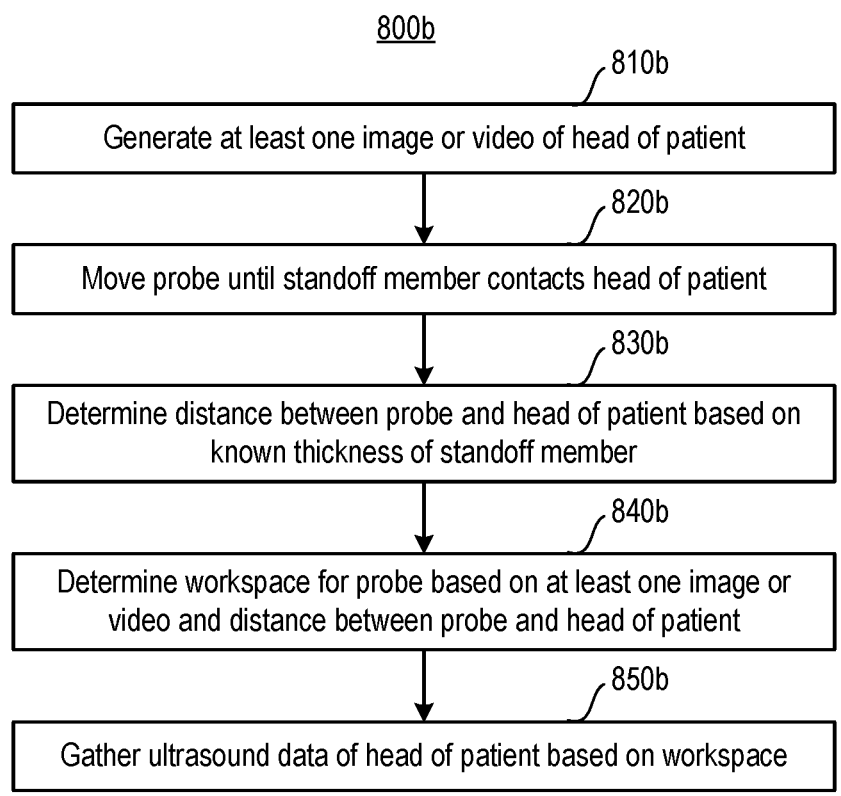
FIG. 8B is a process flow diagram illustrating a method for registering a device including a probe when an enclosure covers the device according to various arrangements.

The standoff member 820 (and the probe contact portion 815) may have a known thickness such that the controller of the device 102 can take into account the fixed parameter during registration. In that regard, FIG. 8B is a process flow diagram illustrating a method 800*b* for registering the device 102 when the enclosure body 810 covers the device 102 according to various arrangements. The method 800*b* may be performed by the controller (e.g., the processing circuit) of the device 102. In other arrangements the enclosure 800 does not include the standoff member 820.

At 810*b*, the controller configures the camera 105 to generate at least one image or video of the head of the subject. At 820*b*, the controller moves the probe 104 until the standoff member 820 contacts the head of the subject. At 830b, the controller determines a distance between the probe 104 and the head of the subject based on a known thickness of the standoff member 820. At 840b, the controller determines a workspace for the probe 104 based on the at least one image or video and the distance between the probe 104 and the head of the subject. At 850b, the controller configures the probe 104 to gather data of the subject based on (within) the workspace.

Figure 9:
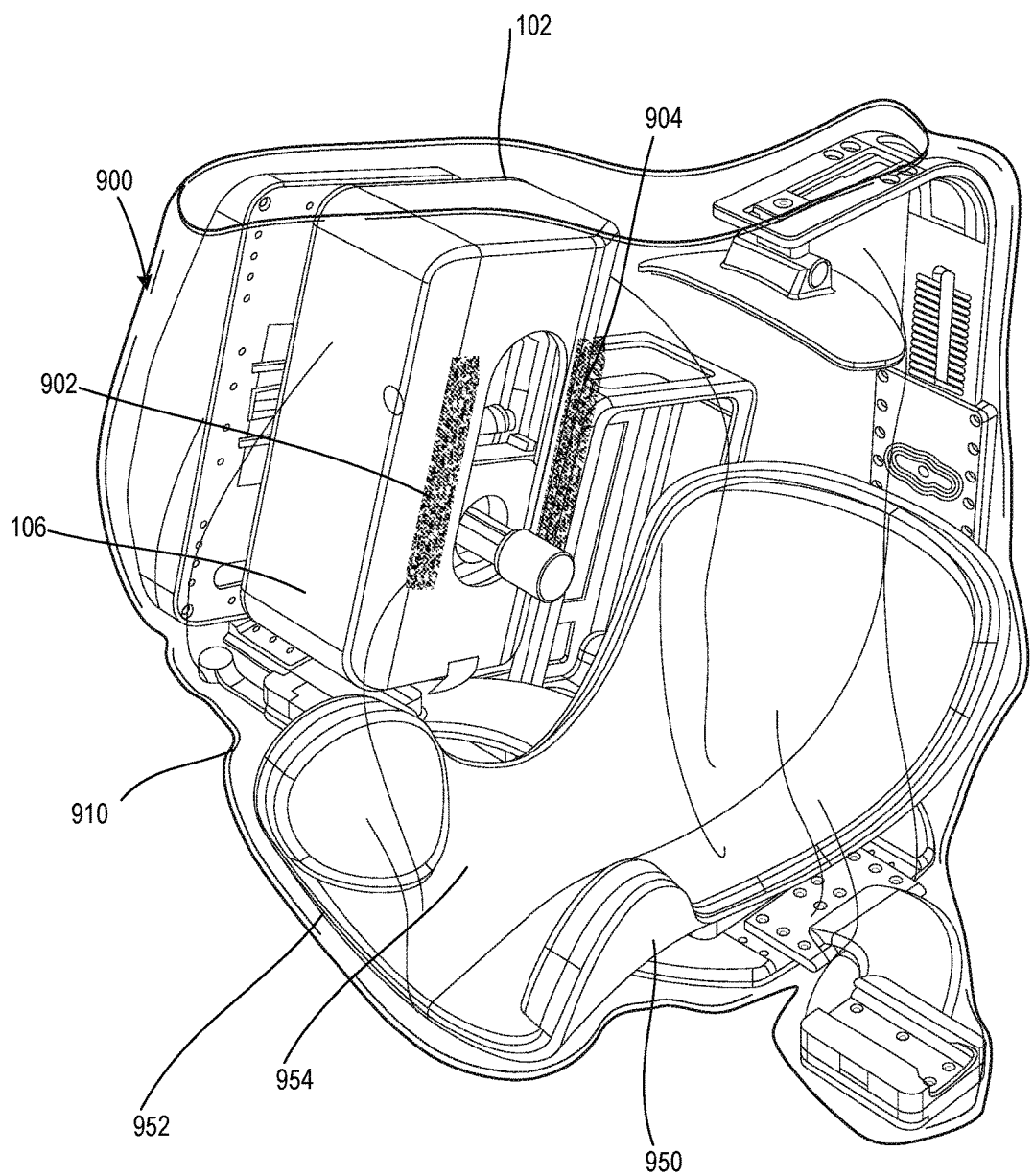
FIG. 9 shows a perspective view of an enclosure covering a headset system including a device including a probe according to various arrangements.

FIG. 9 shows a perspective view of an enclosure 900 covering a headset system 950 including the device 102 according to various arrangements. Referring to FIGS. 1A-9, the enclosure 900 may include an enclosure body 910 such as but not limited to, the enclosure body 110 to provide ingress protection against liquid and particles for the entire headset system 950, including the device 102. For example, the enclosure body 910 is shaped so that the enclosure body 910 can cover the entire headset system 950. The housing 106 (e.g., at portions 902 and 904 and/or the interior surface of the enclosure body 910 (at areas corresponding to the portions 902 and 904) may include adhesives, a hook-and-loop fastener (e.g., Velcro®), or another suitable attachment mechanism for attaching a designated portion of the enclosure body 910 to the housing 106. The subject can lay into the cradle 952 after the enclosure 900 is attached to and covers the entire headset system 950. The enclosure body 910 may include a portion (not shown) configured to be laid under the headset system 950 such that when the subject's head is in the cradle 952, the enclosure body 910 is pinched against a bottom of the headset system 950 and a surface on which the headset system 950 is laid. A padding 954 of the cradle 952 may be permanently or removably attached to the interior surface or the exterior surface of the enclosure body 910, for sanitation purposes.

In some arrangements, an enclosure has a zipper configuration. For example, a slider body may be fixed to the probe 104 and moves with the probe 104. As the probe 104 moves in the X-Y plane, the slider body moves to join or separate teeth on the enclosure, such that the teeth open at the probe 104, but remain closed above and below the probe 104. The teeth can form a seal with each other, the probe 104, and the slider body to provide ingress protection against particles and liquid.

The above used terms, including "held fast," "mount," "attached," "coupled," "affixed," "connected," "secured," and the like are used interchangeably. In addition, while certain arrangements have been described to include a first element as being "coupled" (or "attached," "connected," "fastened," etc.) to a second element, the first element may be directly coupled to the second element or may be indirectly coupled to the second element via a third element.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. All structural and functional equivalents to the elements of the various aspects described throughout the previous description that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

It is understood that the specific order or hierarchy of steps in the processes disclosed is an example of illustrative approaches. Based upon design preferences, it is understood that the specific order or hierarchy of steps in the processes may be rearranged while remaining within the scope of the previous description. The accompanying method claims present elements of the various steps in a sample order, and are not meant to be limited to the specific order or hierarchy presented.

The previous description of the disclosed implementations is provided to enable any person skilled in the art to make or use the disclosed subject matter. Various modifications to these implementations will be readily apparent to those skilled in the art, and the generic principles defined herein may be applied to other implementations without departing from the spirit or scope of the previous description. Thus, the previous description is not intended to be limited to the implementations shown herein but is to be accorded the widest scope consistent with the principles and novel features disclosed herein.

The various examples illustrated and described are provided merely as examples to illustrate various features of the claims. However, features shown and described with respect to any given example are not necessarily limited to the associated example and may be used or combined with other examples that are shown and described. Further, the claims are not intended to be limited by any one example.

The foregoing method descriptions and the process flow diagrams are provided merely as illustrative examples and are not intended to require or imply that the steps of various examples must be performed in the order presented. As will be appreciated by one of skill in the art the order of steps in the foregoing examples may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the examples disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The hardware used to implement the various illustrative logics, logical blocks, modules, and circuits described in connection with the examples disclosed herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In some exemplary examples, the functions described may be implemented in hardware, software, firmware, or any combination thereof. If implemented in software, the functions may be stored as one or more instructions or code on a non-transitory computer-readable storage medium or non-transitory processor-readable storage medium. The steps of a method or algorithm disclosed herein may be embodied in a processor-executable software module which may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer program product.

The preceding description of the disclosed examples is provided to enable any person skilled in the art to make or use the present disclosure. Various modifications to these examples will be readily apparent to those skilled in the art, and the generic principles defined herein may be applied to some examples without departing from the spirit or scope of the disclosure. Thus, the present disclosure is not intended to be limited to the examples shown herein but is to be accorded the widest scope consistent with the following claims and the principles and novel features disclosed herein.

What is claimed is:

1. An enclosure for an acoustic energy device to be used on a subject, the device including a probe supported by a housing, the housing defining a cavity through which the probe protrudes, and the probe configured to move within the cavity and directly contact the subject, the enclosure comprising:
    a removable enclosure body, wherein the enclosure body is configured to enclose at least a portion of the housing while covering the cavity; and
    a probe interaction portion in the enclosure body, wherein the probe interaction portion defines a first hole configured to receive at least a portion of the probe such that the probe is configured to extend through the enclosure body via the first hole and directly contact the subject when the enclosure body covers the cavity.

2. The enclosure of claim 1, wherein the first hole forms a seal around the probe when the enclosure body encloses at least the portion of the housing.

3. The enclosure of claim 2, wherein the first hole is configured to be operatively engaged with the probe to form the seal around the probe via at least one of:
    an elastic band around the first hole;
    a two-piece snap ring;
    an adhesive collar;
    a flap portion; and
    a strap.

4. The enclosure of claim 2, wherein
    the enclosure further comprises a first marker, wherein at least one of:
        the first marker is printed on the enclosure body;
        the first marker is attached to an exterior surface of the enclosure body via first adhesives, the exterior surface facing away from the housing when the enclosure covers the housing; and
        the first marker is attached to an interior surface of the enclosure body via second adhesives, the interior surface facing the housing when the enclosure body encloses at least the portion of the housing.

5. The enclosure of claim 4, wherein
    the first marker has a shape of a ring around the first hole,
    a stretchable portion of the enclosure body is between the first marker and the first hole, and
    the stretchable portion forms the seal around the probe by providing a friction fit with the probe to prevent liquid and particles from entering into the cavity.

6. The enclosure of claim 5, wherein the first marker is made of a material that provides rigidity to the stretchable portion.

7. The enclosure of claim 5, wherein the first marker comprises a gel reservoir for storing gel configured to facilitate transmission of the acoustic energy.

8. The enclosure of claim 1, wherein the probe interaction portion includes an inner surface of the enclosure body comprising an adhesive configured to attach the probe interaction portion to a surface of the probe.

9. The enclosure of claim 1, wherein
    the enclosure body comprises a first portion around the first hole, the first portion forming a pocket around the cavity when the enclosure body encloses at least the portion of the housing.

10. The enclosure of claim 9, wherein
    the first portion forms a seal around the probe by providing a friction fit with the probe to prevent liquid and particles from entering into the cavity, and
    the friction fit is created as the probe is inserted through the first hole, causing the first portion to stretch to form the seal around the probe due to differences of dimensions of the first hole and corresponding dimensions of the probe.

11. The enclosure of claim 9, wherein
    the enclosure body further comprises a second portion different from the first portion, and
    the first portion and the second portion are made of different materials.

12. The enclosure of claim 1, wherein the enclosure further comprises at least one second hole configured to receive a camera of the device, and the camera protrudes from the at least one second hole when the enclosure body encloses at least the portion of the housing.

13. The enclosure of claim 12, wherein the at least one second hole comprises two holes, wherein the camera protrudes from one of the two holes when the enclosure body encloses at least the portion of the housing.

14. The enclosure of claim 12, wherein the at least one second hole is formed by cutting at least a portion of the enclosure body.

15. The enclosure of claim 12, wherein the enclosure further comprises a marker, and the marker is positioned to indicate that the at least one second hole is for the camera, and at least one of:
   the marker is printed on the enclosure body;
   the marker is attached to an exterior surface of the enclosure body via first adhesives, the exterior surface facing away from the housing when the enclosure body encloses at least the portion of the housing; and
   the marker is attached to an interior surface of the enclosure body via second adhesives, the interior surface facing the housing when the enclosure body encloses at least the portion of the housing.

16. The enclosure of claim 1, wherein the enclosure further comprises a fastening mechanism configured to removably secure the enclosure to the housing, wherein the fastening mechanism comprises at least one of:
   an elastic band;
   a hook-and-loop fastener;
   adhesive strips; and
   strings.

17. The enclosure of claim 1, wherein the enclosure further comprises a fastening base configured to removably secure the enclosure to the housing, wherein the fastening base comprises an adhesive base.

18. The enclosure of claim 17, wherein the enclosure body is configured to bulge in at least one of an outward direction away from the cavity or an inward direction toward the cavity.

19. The enclosure of claim 17, wherein the fastening base is made from a foam and is configured to be removably secured to a front surface of the housing such that at least a portion of the front surface of the housing is uncovered by the enclosure body.

20. The enclosure of claim 17, wherein the fastening base surrounds the cavity when the fastening base is removably secured to the housing.

21. The enclosure of claim 1, wherein the enclosure further comprises:
   a first marker positioned to indicate that the first hole is for the probe;
   at least one second hole comprising two second holes; and
   a fastening mechanism configured to removably secure the enclosure to the housing, wherein
      the enclosure body is configured as a disposable bag having a rectangular shape,
      the first hole is positioned in an approximated center of the rectangular shape,
      the first marker has a shape of a ring that is concentric with the first hole,
      each of the second holes is formed by cutting off a corner of the rectangular shape, and
      the fastening mechanism is at an edge of the rectangular shape.

22. The enclosure of claim 1, wherein
   the enclosure body comprises two or more tabs,
   each of the two or more tabs comprises adhesives, and
   the two or more tabs are configured to releasably attach to the housing via the adhesives.

23. The enclosure of claim 1, wherein
   the enclosure body is made of at least one biocompatible material suitable for contacting a human body, and
   the at least one biocompatible material comprises one or more of polyethylene (PE), polypropylene (PE), polycarbonate (PC), polyurethane (PU), polyetherimide (PEI), polyvinyl chloride (PVC), and polyether ether ketone (PEEK).

24. The enclosure of claim 1, wherein the enclosure body is made of an elastic material that can be form-fitted to the portion of the housing when the enclosure body encloses the at least the portion of the housing.

25. The enclosure of claim 1, wherein the enclosure body is made of a material that provides ingress protection against liquid and particles to the cavity.

26. A method for providing an enclosure for an acoustic energy device to be used on a subject, the device including a probe supported by a housing, the housing defining a cavity through which the probe protrudes, and the probe configured to move within the cavity and directly contact the subject, the method comprising:
   manufacturing a removable enclosure body, wherein the enclosure body is configured to enclose at least a portion of the housing while covering the cavity; and
   installing a probe interaction portion in the enclosure body, wherein the probe interaction portion defines a first hole configured to receive at least a portion of the probe such that the probe is configured to extend through the enclosure body via the first hole and directly contact the subject when the enclosure body covers the cavity.

27. An acoustic energy device to be used on a subject, comprising:
   a probe;
   a housing supporting the probe, wherein the housing defines a cavity through which the probe protrudes, and wherein the probe is configured to move within the cavity and directly contact the subject;
   a disposable enclosure, comprising:
      a removable enclosure body, wherein the enclosure body is configured to enclose at least a portion of the housing while covering the cavity; and
      a probe interaction portion in the enclosure body, wherein the probe interaction portion defines a first hole configured to receive at least a portion of the probe such that the probe is configured to extend through the enclosure body via the first hole and directly contact the subject when the enclosure body covers the cavity.

\* \* \* \* \*